(12) United States Patent
Herron et al.

(10) Patent No.: US 8,309,731 B2
(45) Date of Patent: Nov. 13, 2012

(54) ELECTRONIC DEVICE INCLUDING PHENANTHROLINE DERIVATIVE

(75) Inventors: Norman Herron, Newark, DE (US);
Mark A. Guidry, Wilmington, DE (US);
Vsevolod Rostovtsev, Swarthmore, PA (US); Weiying Gao, Landenberg, PA (US); Ying Wang, Wilmington, DE (US); Yulong Shen, Wilmington, DE (US); Jeffrey A. Merlo, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/299,845

(22) Filed: Nov. 18, 2011

(65) Prior Publication Data

US 2012/0065402 A1 Mar. 15, 2012

(51) Int. Cl.
*C07D 471/04* (2006.01)
*C07D 519/00* (2006.01)
(52) U.S. Cl. ........................................ 546/88
(58) Field of Classification Search .................... 546/88
See application file for complete search history.

(56) References Cited

U.S. PATENT DOCUMENTS

| 5,077,142 A | 12/1991 | Sakon et al. |
| 5,393,614 A | 2/1995 | Nakada |

(Continued)

FOREIGN PATENT DOCUMENTS

EP          341859 A1      11/1989

(Continued)

OTHER PUBLICATIONS

Dietrich-Buchecker et al., "Direct Synthesis of Disubstituted Aromatic Polyimine Chelates," Tetrahedron Letters, 1982, vol. 23 (50), pp. 5291-5294.

(Continued)

*Primary Examiner* — Calvin Lee
*Assistant Examiner* — Monica D. Harrison

(57) ABSTRACT

There is provided an organic electronic device having an anode, a hole injection layer, a photoactive layer, an electron transport layer, and a cathode. At least one of the photoactive layer and the electron transport layer includes a compound having Formula I

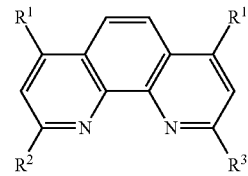

Formula I where:
$R^1$ is the same or different and can be phenyl, biphenyl, naphthyl, naphthylphenyl, triphenylamino, or carbazolylphenyl;
and one of the following conditions is met:
(i) $R^2 = R^3$ and is H, phenyl, biphenyl, naphthyl, naphthylphenyl, arylanthracenyl, phenanthryl, triphenylamino, or carbazolylphenyl; or
(ii) $R^2$ is H or phenyl; and
$R^3$ is phenyl, biphenyl, naphthyl, naphthylphenyl, arylanthracenyl, phenanthryl, triphenylamino, and carbazolylphenyl;
When both $R^1$ are phenyl, $R^2$ and $R^3$ can be 2-naphthyl, naphthylphenyl, arylanthracenyl, 9-phenanthryl, triphenylamino, or m-carbazolylphenyl.

1 Claim, 1 Drawing Sheet

U.S. PATENT DOCUMENTS

| | | | |
|---|---|---|---|
| 6,303,238 | B1 | 10/2001 | Thompson et al. |
| 6,524,728 | B1 | 2/2003 | Kijima et al. |
| 6,670,645 | B2 | 12/2003 | Grushin et al. |
| 7,119,204 | B2 | 10/2006 | Lecloux et al. |
| 7,186,469 | B2 | 3/2007 | Shibanuma et al. |
| 2004/0102577 | A1 | 5/2004 | Hsu et al. |
| 2004/0127637 | A1 | 7/2004 | Hsu et al. |
| 2005/0205860 | A1 | 9/2005 | Hsu et al. |
| 2006/0017050 | A1 | 1/2006 | Hasegawa et al. |
| 2006/0115676 | A1* | 6/2006 | Igawa et al. .............. 428/690 |
| 2006/0134460 | A1 | 6/2006 | Kondakova et al. |
| 2006/0134464 | A1 | 6/2006 | Nariyuki |
| 2006/0204784 | A1 | 9/2006 | Begley et al. |
| 2007/0026257 | A1 | 2/2007 | Begley et al. |
| 2007/0037983 | A1 | 2/2007 | Nomura et al. |
| 2007/0176544 | A1 | 8/2007 | Koike et al. |
| 2009/0001327 | A1 | 1/2009 | Werner et al. |
| 2009/0162644 | A1 | 6/2009 | Ricks et al. |
| 2009/0242877 | A1 | 10/2009 | Kondakov |

FOREIGN PATENT DOCUMENTS

| | | |
|---|---|---|
| EP | 564224 A2 | 5/1997 |
| EP | 1013740 A2 | 6/2000 |
| EP | 1097981 A2 | 5/2001 |
| EP | 1786050 A1 | 5/2007 |
| EP | 2161272 A1 | 3/2010 |
| JP | 61041152 A | 2/1986 |
| JP | 2001110572 A | 4/2001 |
| JP | 2001267080 A | 9/2001 |
| JP | 2002352961 A | 12/2002 |
| WO | 0070655 A2 | 11/2000 |
| WO | 0141512 A1 | 6/2001 |
| WO | 0230159 A1 | 4/2002 |
| WO | 0243449 A1 | 5/2002 |
| WO | 03008424 A1 | 1/2003 |
| WO | 03040257 A1 | 5/2003 |
| WO | 03063555 A1 | 7/2003 |
| WO | 03079737 A2 | 9/2003 |
| WO | 03091688 A2 | 11/2003 |
| WO | 2004016710 A1 | 2/2004 |
| WO | 2006011090 A1 | 2/2006 |
| WO | 2007145979 A2 | 12/2007 |

OTHER PUBLICATIONS

Dietrich-Buchecker, Christiane et al., Selective and efficient synthesis of di-, tri- and tetrasubstituted 1,10-phenanthrolines, Tetrahedron Letters, 1999, 3395-3396, 40, Elsevier Science Ltd.

Giebeler, C. et al., The photovoltaic effect in poly(p-phenylene-2,3'-bis(3,2'-diphenyl)-quinoxaline-7-7'-diyl), Optical Materials, Jan. 1998, 99-103, 9, Elsevier Science B.V.

Gustafsson et al.—Flexible Light-Emitting Diodes Made From Soluble Conducting Polymers, Nature 1992 vol. 357 pp. 477-479.

Jin, Sung-Ho et al., Blue electroluminescence in blend of polymers containing carbazole and 1,3,4-oxadiazole units, Thin Solid Films, 2000, 255-258, 363, Elsevier Science S.A.

Limburg, W. et al., Electronic Transport Properties of Molecularly Doped Polymers—Some Substituted Triarylmethanes, Organic Coatings and Plastics, Chemistry, 1978, 534-539, 38.

Markus et al—Electronics and Nucleonics Dictionary, pp. 470-471 & 476 (McGraw-Hill 1966).

O'Brien, D. et al., Use of poly(phenyl quinoxaline) as an electron transport material in polymer light-emitting diodes, Appl. Phys. Lett., Aug. 12, 1996, 881-883, 69(7), American Institute of Physics.

Rehahn, Matthias et al, Synthesis, solution properties and conversion of poly(2,9-o-phenanthroline-alt-(2'5'-dihexyl)-4,4''-p-terphenylene)s into soluble, well-defined copper(I) and silver (I) complex polymers, Macromol. Chem. Phys., 1998, 127-140, 199, Huthig & Wepf Verlag, Zug.

Sun, Li-Xian et al., PVC membrane lithium-selective electrodes based on oligomethylene-bridged bis-1,10-phenanthroline derivatives, Analytica Chimica Acta, 1996, 57-64, 329, Elsevier Science B.V.

Wang—Photoconductive Materials, Kirk-Othmer Encyclopedia of Chemical Technology, Fourth Edition, 1996, vol. 18 pp. 837-860.

Yamamoto, Takakazu et al., Preparation and Properties of pi-Conjugated Poly(1,10-phenanthroline03,8-diyl), Chemistry Letters, 1995, pp. 785-786.

Yamamoto, Takakazu et al., Preparation of New Electron-Accepting-Conjugated Polyquinoxalines. Chemical and Electrochemical Reduction, Electrically Conducting Properties, and Use in Light-Emitting Diodes, J. Am. Chem. Soc., 1996, 3930-3937, 118, American Chemical Society.

Zotti et al., Electrochemical, Conductive and Magnetic Properties of 2,7-Carbazole-based Conjugated Polymers, Macromolecules, vol. 35, Feb. 7, 2002, pp. 2122-2128.

International Search Report, Korean Intellectual Property Office, Daejeong, KR; Application No. PCT/US2009/069184, PCT counterpart to U.S. Appl. No. 12/644,362; Hyun Shik Oh, Authorized Officer, 20100805.

* cited by examiner

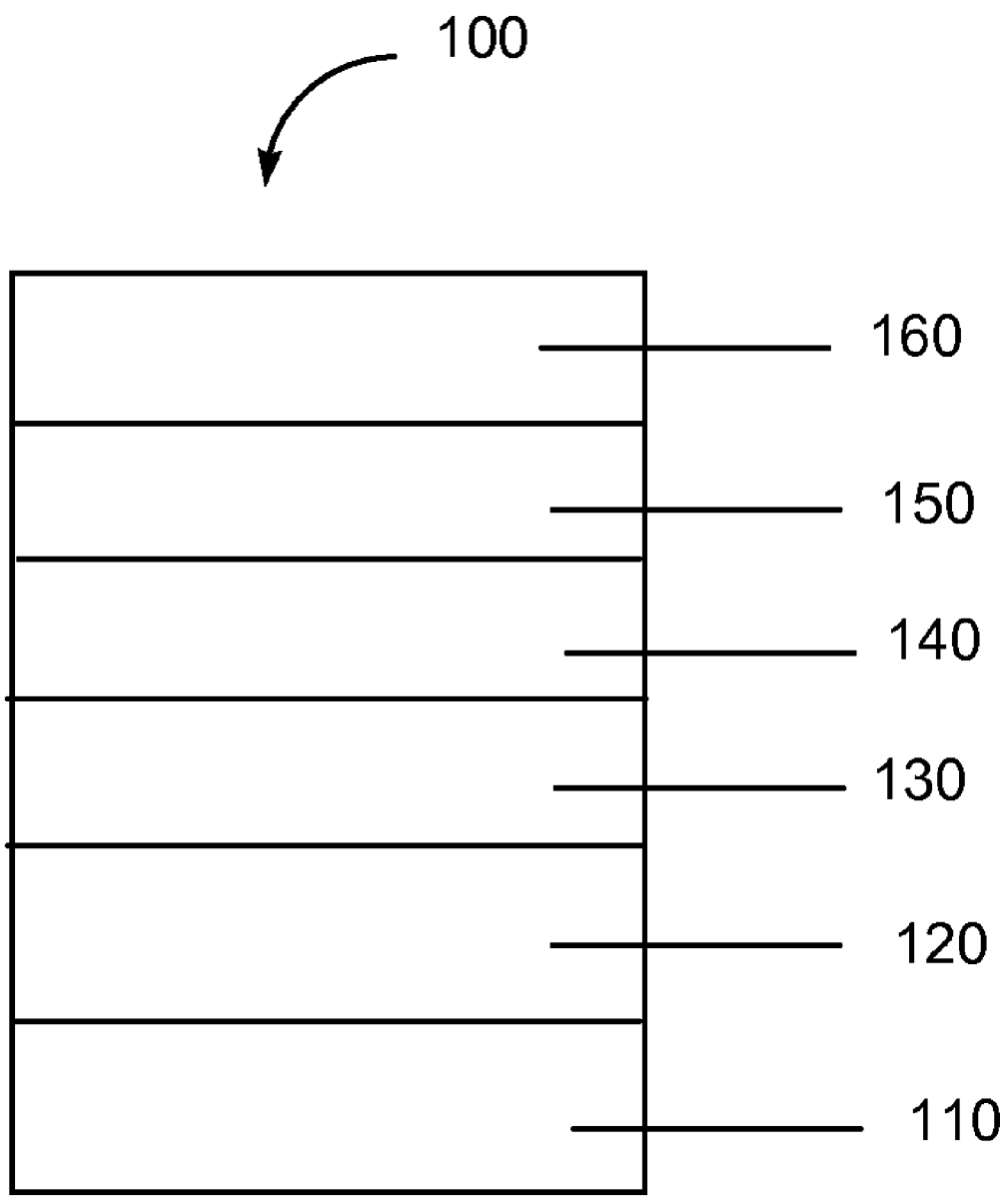

ELECTRONIC DEVICE INCLUDING PHENANTHROLINE DERIVATIVE

RELATED APPLICATION DATA

This application claims priority under 35 U.S.C. §120 from U.S. patent application Ser. No. 12/644,362, filed Dec. 22, 2009 (incorporated by reference herein in its entirety), which in turn claimed priority under 35 U.S.C. 119(e) from U.S. Provisional Application No. 61/139,811 filed on Dec. 22, 2011, which is incorporated by reference herein in its entirety.

BACKGROUND INFORMATION

1. Field of the Disclosure

This disclosure relates in general to organic electronic devices including at least one layer having a phenanthroline derivative.

2. Description of the Related Art

In organic photoactive electronic devices, such as organic light emitting diodes ("OLED"), that make up OLED displays, the organic active layer is sandwiched between two electrical contact layers in an OLED display. In an OLED, the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode. Charge transport materials can also be used as hosts in combination with the photoactive materials.

There is a continuing need for new materials for electronic devices.

SUMMARY

There is provided an organic electronic device comprising an anode, a hole injection layer, a photoactive layer, an electron transport layer, and a cathode, wherein at least one of the photoactive layer and the electron transport layer comprises a compound having Formula I

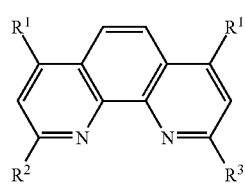

Formula I where:
R$^1$ is the same or different and is selected from the group consisting of phenyl, biphenyl, naphthyl, naphthylphenyl, triphenylamino, and carbazolylphenyl;

and one of the following conditions is met:
(i) R$^2$=R$^3$ and is selected from the group consisting of H, phenyl, biphenyl, naphthyl, naphthylphenyl, arylanthracenyl, phenanthryl, triphenylamino, and carbazolylphenyl; or
(ii) R$^2$ is selected from the group consisting of H and phenyl;
R$^3$ is selected from the group consisting of phenyl, biphenyl, naphthyl, naphthylphenyl, arylanthracenyl, phenanthryl, triphenylamino, and carbazolylphenyl;
with the proviso that when both R$^1$ are phenyl, R$^2$ and R$^3$ are selected from the group consisting of biphenyl, 2-naphthyl, naphthylphenyl, arylanthracenyl, 9-phenanthryl, triphenylamino, and m-carbazolylphenyl.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 1 includes an illustration of an exemplary organic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Phenanthroline Derivatives, the Electronic Device, and finally Examples.

1. Definitions and Clarification of Terms

Before addressing details of embodiments described below, some terms are defined or clarified.

The term "alkyl" is intended to mean a group derived from an aliphatic hydrocarbon.

The term "aryl" is intended to mean a group derived from an aromatic hydrocarbon. The term "aromatic compound" is intended to mean an organic compound comprising at least one unsaturated cyclic group having delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although light-emitting materials may also have some charge transport properties, the term "charge transport layer, material, member, or structure" is not intended to include a layer, material, member, or structure whose primary function is light emission.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "host material" is intended to mean a material, usually in the form of a layer, to which a dopant may or may not be added. The host material may or may not have electronic characteristic(s) or the ability to emit, receive, or filter radiation.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device," or sometimes just "electronic device," is intended to mean a device including one or more organic semiconductor layers or materials.

The term "photoactive" is intended to mean a material or layer that emits light when activated by an applied voltage (such as in a light emitting diode or chemical cell) or responds to radiant energy and generates a signal with or without an applied bias voltage (such as in a photodetector).

Unless otherwise indicated, all groups can be unsubstituted or substituted. Unless otherwise indicated, all groups can be linear, branched or cyclic, where possible. In some embodiments, the substituents are selected from the group consisting of alkyl, alkoxy, and aryl.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Phenanthroline Compound

Electron transport materials have been used as host materials in photoactive layers and in electron transport layers. Electron transport materials based on metal complexes of quinoline ligands, such as with Al, Ga, or Zr, have been used in these applications. However, there are several disadvantages. The complexes can have poor atmospheric stability when used as hosts. It is difficult to plasma clean fabricated parts employing such metal complexes. The low triplet energy leads to quenching of phosphorescent emission of >2.0 eV energy. Bathophenanthroline materials have also been used as electron transport materials. However, processing characteristics, especially solubility, are frequently unsatisfactory for some applications as a host material.

The phenanthroline derivatives described herein have new substitution patterns over previously reported materials and a general synthetic approach to the diverse substitution arrangements has been developed. In some embodiments, the phenanthroline derivatives are useful as solution processable electron dominated hosts for OLED devices or as electron transport materials suitable for n-doping in OLED devices having a thick electron transport layer. The resulting devices have low current leakage. The good electron mobility and high Tg allow for long lived and high efficiency devices. In some embodiments, the materials are useful in any printed electronics application including photovoltaics and TFTs.

The phenanthroline derivative compounds described herein have Formula I

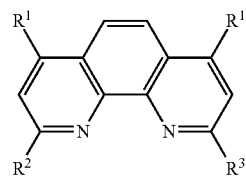

Formula I where:
  $R^1$ is the same or different and is selected from the group consisting of phenyl, biphenyl, naphthyl, naphthylphenyl, triphenylamino, and carbazolylphenyl;
  and one of the following conditions is met:
  (i) $R^2=R^3$ and is selected from the group consisting of H, phenyl, biphenyl, naphthyl, naphthylphenyl, arylanthracenyl, phenanthryl, triphenylamino, and carbazolylphenyl; or
  (ii) $R^2$ is selected from the group consisting of H and phenyl;

R³ is selected from the group consisting of phenyl, biphenyl, naphthyl, naphthylphenyl, arylanthracenyl, phenanthryl, triphenylamino, and carbazolylphenyl; with the proviso that when both R¹ are phenyl, R² and R³ are selected from the group consisting of biphenyl, 2-naphthyl, naphthylphenyl, arylanthracenyl, 9-phenanthryl, triphenylamino, and m-carbazolylphenyl.

The groups referred to above are defined as follows, where the dashed lines represent possible points of attachment.

biphenyl:

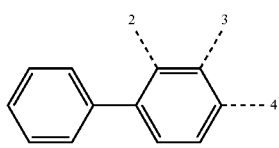

naphthyl:

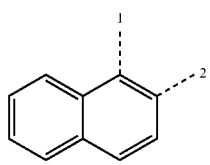

naphthylphenyl:

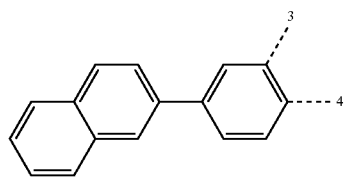

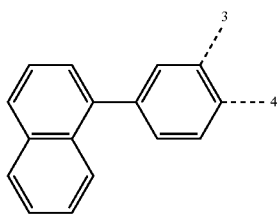

phenanthryl:

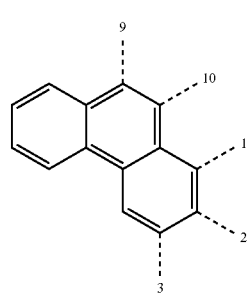

triphenylamino:

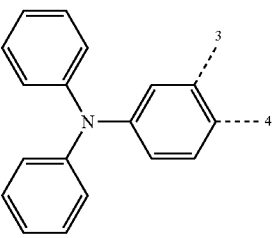

carbazolylphenyl:

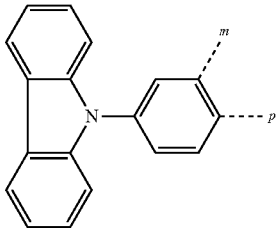

arylanthracenyl:

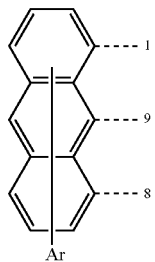

The new phenanthroline derivatives can have enhanced solubility, high thermal stability (high Tg>100 C) and good electron mobility. The compounds demonstrate good air stability. They can be used as electron transport materials for n-doped OLED devices as well as electron dominated hosts (for both fluorescent and phosphorescent emitters) for emissive layers in solution processed OLED devices.

In some embodiments, the phenanthroline compounds are symmetrical, where both R¹ are the same and R²=R³. In some embodiments, R¹=R²=R³. In some embodiments, the phenanthroline compounds are non-symmetrical, where the two R¹ groups are different, R²≠R³, or both.

In some embodiments, the R¹ groups are the same and are selected from the group consisting of biphenyl, naphthyl, naphthylphenyl, triphenylamino, and carbazolylphenyl. In some embodiments, the R¹ groups are selected from the group consisting of phenyl, triphenylamino, and carbazolylphenyl. In some embodiments, the R¹ groups are selected from the group consisting of 4-triphenylamino and m-carbazolylphenyl.

In some embodiments, R²=R³ and is selected from the group consisting of triphenylamino, naphthylphenyl, arylanthracenyl, and m-carbazolylphenyl. In some embodiments, the arylanthracenyl group has the structure

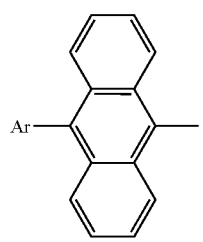

where Ar is selected from the group consisting of phenyl, naphthyl, and naphthylphenyl.

In some embodiments, $R^2$=H and $R^3$ is selected from the group consisting of phenyl, biphenyl, naphthylphenyl, arylanthracenyl, triphenylamino, and carbazolylphenyl.

In some embodiments, the phenanthroline compound is selected from the group consisting of Compound 1 through Compound 21 shown below.

Compound 1

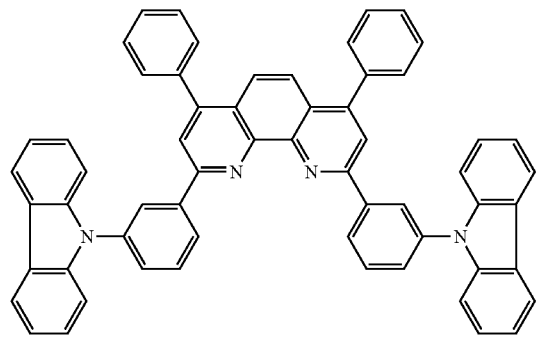

Compound 2

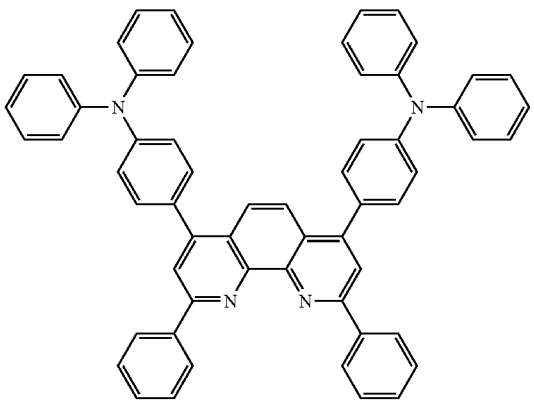

Compound 3

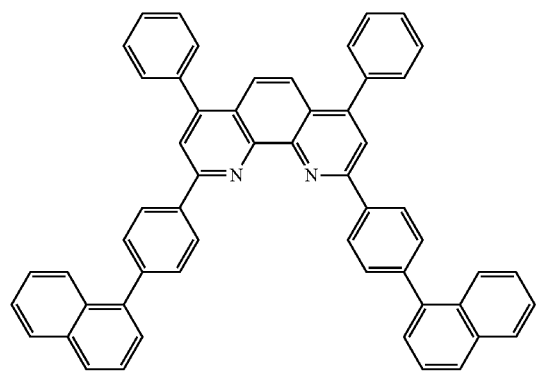

Compound 4

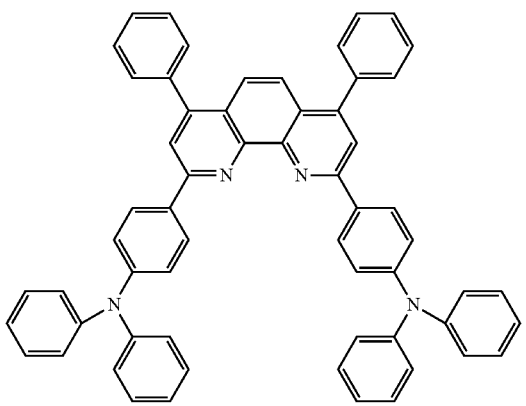

Compound 5

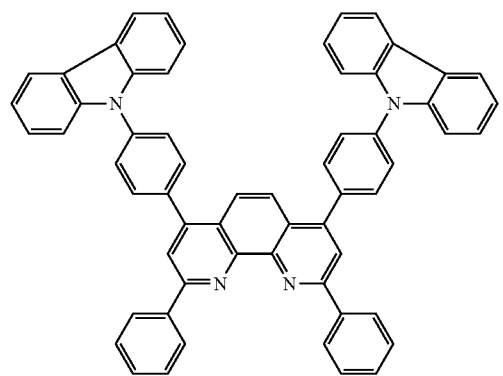

Compound 6

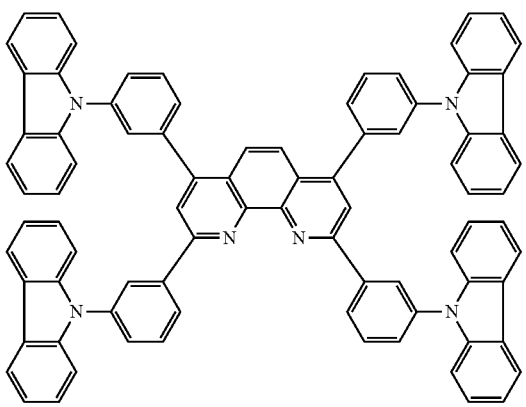

-continued
Compound 7
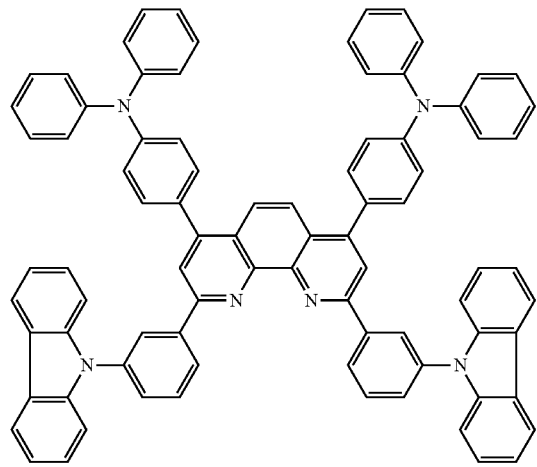
Compound 8
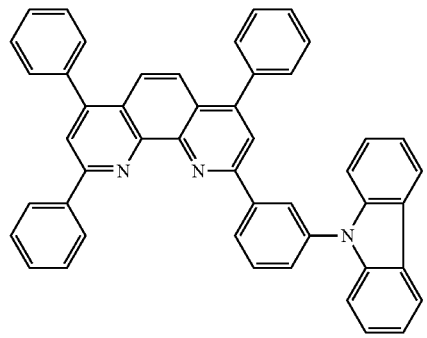
Compound 9
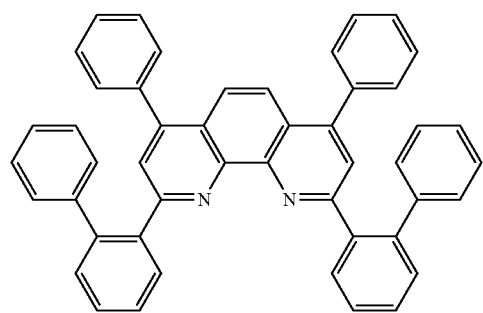
Compound 10
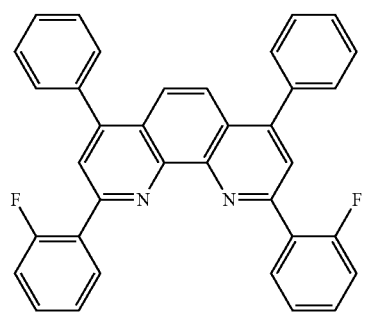
Compound 11
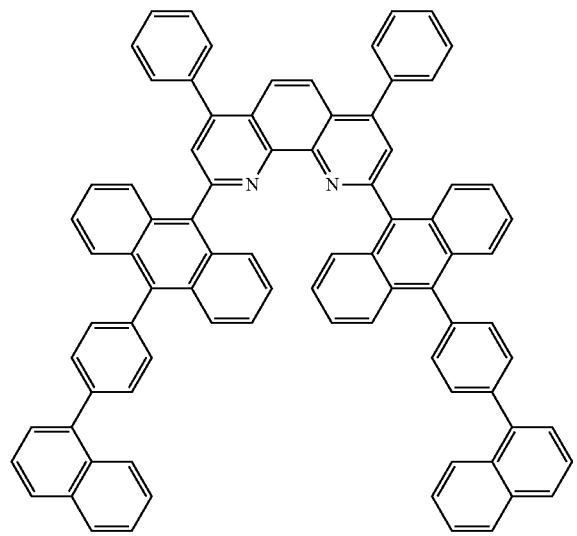

-continued
Compound 12
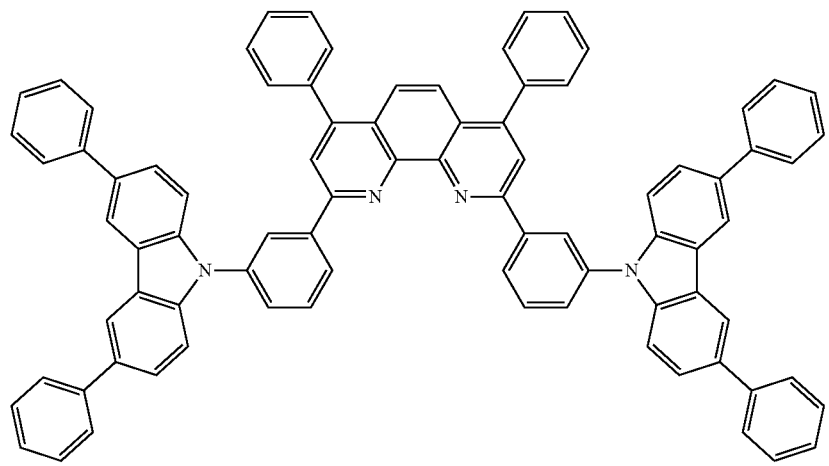
Compound 13
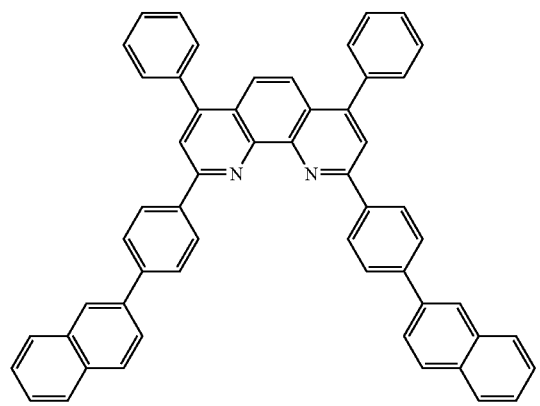
Compound 14
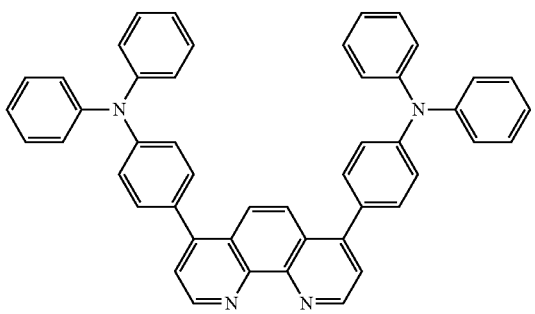
Compound 15
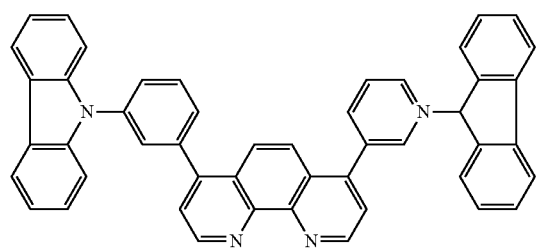
Compound 16
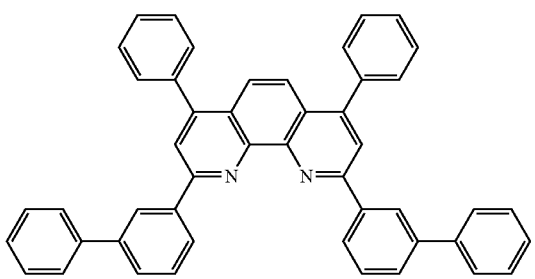
Compound 17
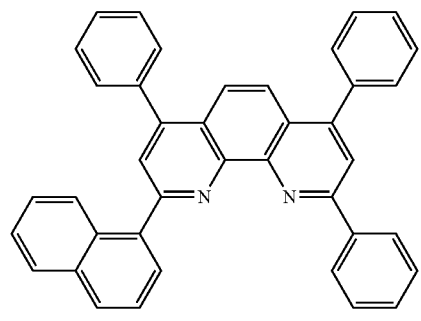
Compound 18
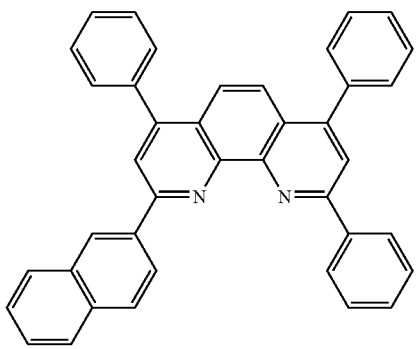

Compound 19

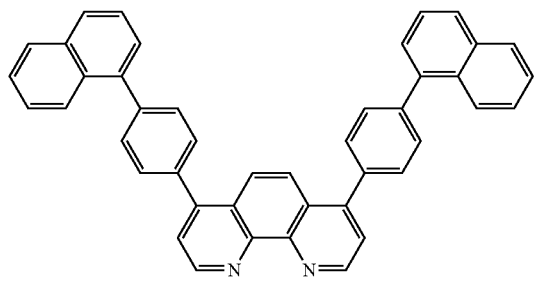

Compound 20

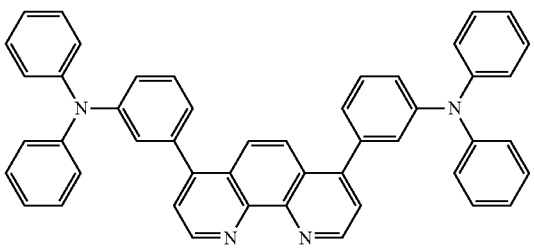

Compound 21

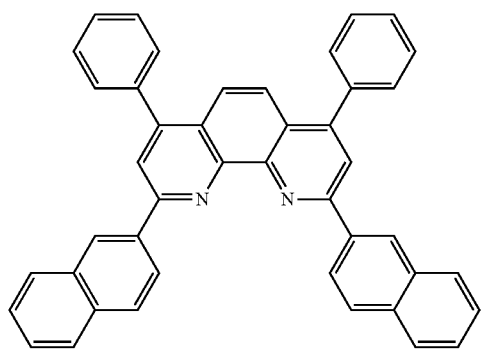

These compounds have the properties shown in Table 1 below.

TABLE 1

Compound Properties

| Compound | Tg, °C. | PL maximum (nm) | Solubility in toluene (mg/ml) |
|---|---|---|---|
| 1 | 172 | 404 | 4.8 |
| 2 | 150 | 434 | 7.6 |
| 3 | 160 | 414/393 | 4.5 |
| 4 | 156 | 444 | 31.3 |
| 5 |  | 409 |  |
| 9 | 131 | 395 | 25.6 |
| 10 |  | 399 | 22.2 |
| 11 |  | 488 | 10.1 |
| 12 | 220 | 429 | 22.8 |
| 13 |  | 400/420 | 2.0 |
| 14 | 133 | 431 |  |
| 15 | 156 | 400 | 20 |
| 16 |  | 354.5 | 0.8[a] |
| 17 | 115 | 392/413 | 4.2 |
| 18 |  | 402 | 2.3 |
| 19 | 140 | 412 |  |
| 20 | 116 | 441 | 32.2 |
| 21 | 147 | 409.5 | 1.0[b] |

PL maximum = maximum peak in photoluminescence emission spectrum
[a]solubility in anisole is 5.0
[b]solubility in anisole is 3.0

The phenanthroline compounds can be made by known synthetic techniques. In some embodiments, the compounds are made by Suzuki coupling of dichloro phenanthrolines with the boronic acid analog of the desired substituent. This is further illustrated in the examples.

3. Electronic Device

Organic electronic devices that may benefit from having one or more layers comprising the blue luminescent materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a buffer layer 120. Adjacent to the buffer layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

In one embodiment, the different layers have the following range of thicknesses: anode 110, 500-5000 Å, in one embodiment 1000-2000 Å; buffer layer 120, 50-2000 Å, in one embodiment 200-1000 Å; hole transport layer 130, 50-2000 Å, in one embodiment 200-1000 Å; photoactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the photoactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

a. Photoactive Layer

The phenanthroline compounds of Formula I are useful as host materials for photoactive materials in layer 140. The compounds can be used alone, or used as a co-host in combination with another host material. These phenanthroline compounds have good solubility for liquid deposition applications. In some embodiments, the phenanthroline compounds are used as a host for blue emissive dopant materials. The ratio of host to dopant is generally in the range of 5:1 to 25:1; in some embodiments, from 10:1 to 20:1. In some embodiments, the photoactive layer consists essentially of a photoactive material and a phenanthroline derivative having Formula I.

In some embodiments, the photoactive dopant materials are electroluminescent and are selected from materials which have red, green and blue emission colors. Electroluminescent materials include small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (AlQ); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly (phenylenevinylenes), polyfluorenes, poly(spirobifluorenes), polythiophenes, poly(p-phenylenes), copolymers thereof, and mixtures thereof.

In some embodiments, the photoactive dopant is a cyclometalated complex of iridium. In some embodiments, the complex has two ligands selected from phenylpyridines, phenylquinolines, and phenylisoquinolines, and a third liqand with is a β-dienolate. The ligands may be unsubstituted or substituted with F, D, alkyl, CN, or aryl groups.

In some embodiments, the photoactive dopant is a polymer selected from the group consisting of poly(phenylenevinylenes), polyfluorenes, and polyspirobifluorenes.

In some embodiments, the photoactive dopant is selected from the group consisting of a non-polymeric spirobifluorene compound and a fluoranthene compound.

In some embodiments, the photoactive dopant is a compound having aryl amine groups. In some embodiments, the photoactive dopant is selected from the formulae below:

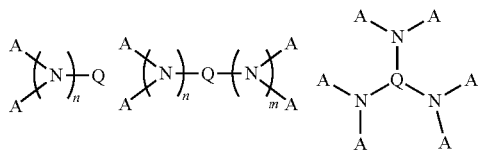

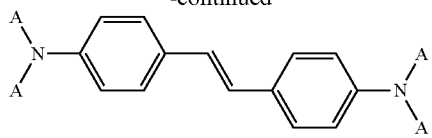

where:

A is the same or different at each occurrence and is an aromatic group having from 3-60 carbon atoms;

Q is a single bond or an aromatic group having from 3-60 carbon atoms;

n and m are independently an integer from 1-6.

In some embodiments of the above formula, at least one of A and Q in each formula has at least three condensed rings. In some embodiments, m and n are equal to 1.

In some embodiments, Q is a styryl or styrylphenyl group.

In some embodiments, Q is an aromatic group having at least two condensed rings. In some embodiments, Q is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, tolyl, naphthyl, and anthracenyl groups.

In some embodiments, the photoactive dopant has the formula below:

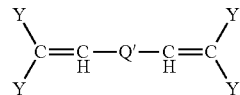

where:

Y is the same or different at each occurrence and is an aromatic group having 3-60 carbon atoms;

Q' is an aromatic group, a divalent triphenylamine residue group, or a single bond.

In some embodiments, the photoactive dopant is an aryl acene. In some embodiments, the photoactive dopant is a non-symmetrical aryl acene.

In some embodiments, the photoactive dopant is a chrysene derivative. The term "chrysene" is intended to mean 1,2-benzophenanthrene. In some embodiments, the photoactive dopant is a chrysene having aryl substituents. In some embodiments, the photoactive dopant is a chrysene having arylamino substituents. In some embodiments, the photoactive dopant is a chrysene having two different arylamino substituents. In some embodiments, the chrysene derivative has a deep blue emission.

In some embodiments, the photoactive dopant is selected from the group consisting of E1 through E10 shown below.

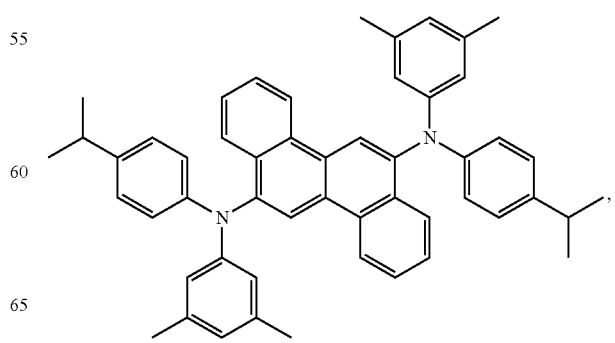

E1

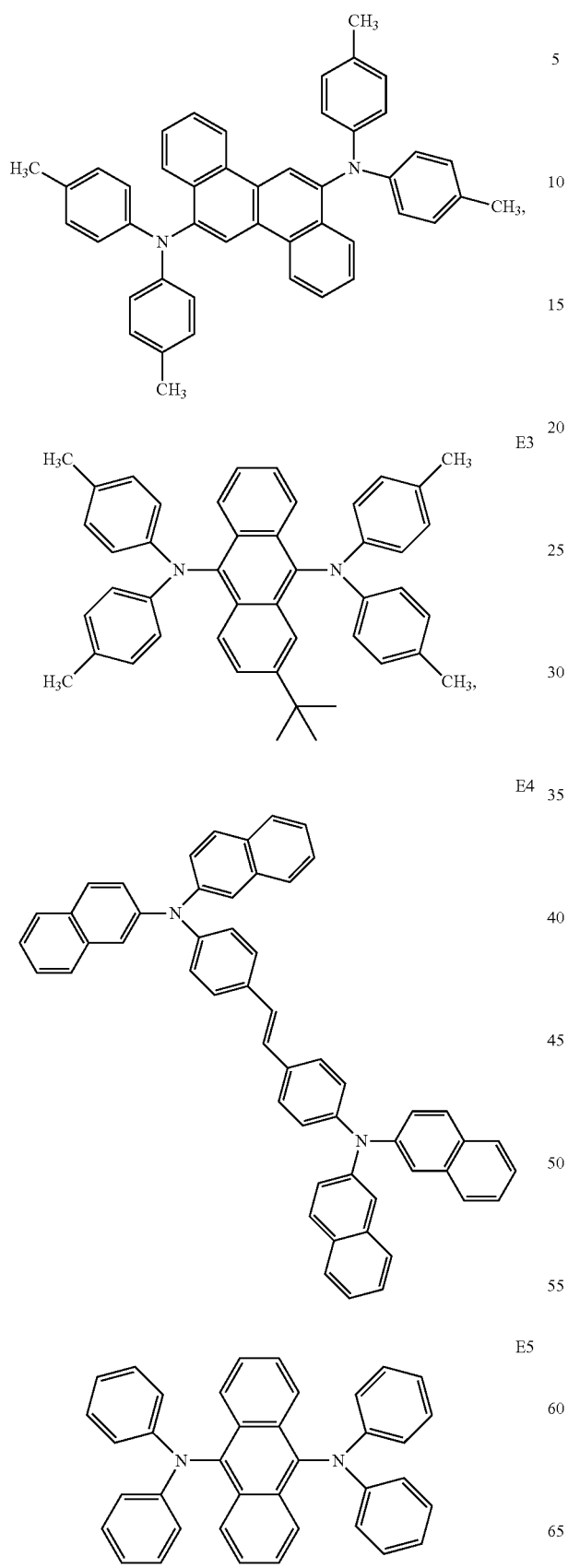
In some embodiments, the phenanthroline derivative compound is used with an additional host material. In some embodiments, the phenanthroline derivative compound is not used as a host in the photoactive layer. Examples of other types of hosts which can be used alone or in combination with the phenanthroline compounds, include, but are not limited to, bis-condensed cyclic aromatic compounds and anthracene derivatives.

In some embodiments the anthracene host compound has the formula:

An-L-An where:
An is an anthracene moiety;
L is a divalent connecting group.

In some embodiments of this formula, L is a single bond, —O—, —S—, —N(R)—, or an aromatic group. In some embodiments, An is a mono- or diphenylanthryl moiety.

In some embodiments, the anthracene host has the formula:

A-An-A where:
An is an anthracene moiety;
A is the same or different at each occurrence and is an aromatic group.

In some embodiments, the A groups are attached at the 9- and 10-positions of the anthracene moiety. In some embodiments, A is selected from the group consisting naphthyl, naphthylphenylene, and naphthylnaphthylene. In some embodiments the compound is symmetrical and in some embodiments the compound is non-symmetrical.

In some embodiments, the anthracene host has the formula:

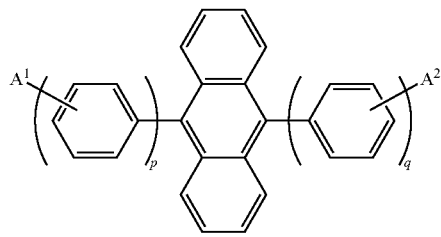

where:
$A^1$ and $A^2$ are the same or different at each occurrence and are selected from the group consisting of H, an aromatic group, and an alkenyl group, or A may represent one or more fused aromatic rings;
p and q are the same or different and are an integer from 1-3. In some embodiments, the anthracene derivative is non-symmetrical. In some embodiments, p=2 and q=1. In some embodiments, at least one of $A^1$ and $A^2$ is a naphthyl group.

In some embodiments, the host is selected from the group consisting of

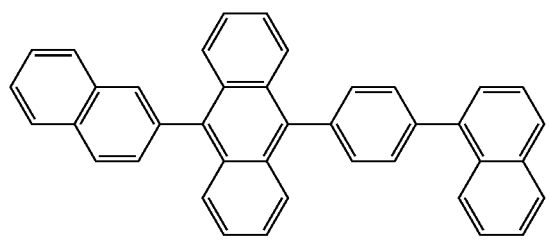

H1

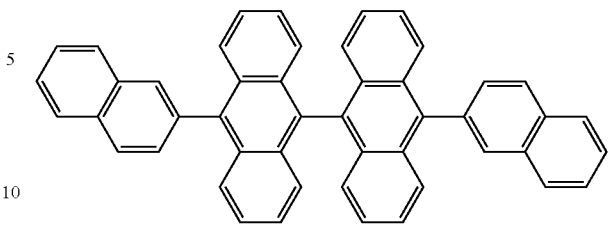

H2 and combinations thereof.

b. Electron Transport Layer

The phenanthroline compounds of Formula I are useful as electron transport materials in layer 150. The compounds can be used alone, or in combination with another electron transport material. As discussed above, the materials have good solubility in many solvents for liquid deposition applications.

In some embodiments, the electron transport layer consists essentially of a phenanthroline derivative having Formula I. In some embodiments, the phenanthroline compound is used in combination with an n-dopant. Examples of such dopants include, but are not limited to, Cs or other alkali metals.

Examples of other electron transport materials which can be used alone or in combination with the phenanthroline compounds include, but are not limited to, metal chelated oxinoid compounds, including metal quinolate derivatives such as tris(8-hydroxyquinolato)aluminum (AlQ), bis(2-methyl-8-quinolinolato)(p-phenylphenolato)aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. The materials may also be used in combination with n-dopants.

c. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

The hole injection layer 120 comprises buffer material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules. They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. Such materials have been described in, for example, published U.S. patent applications 2004-0102577, 2004-0127637, and 2005/205860

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. In some embodiments, the hole transport layer is doped with a p-dopant, such as tetrafluorotetracyanoquinodimethane and perylene-3,4,9,10-tetracarboxylic-3,4,9,10-dianhydride.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, $Li_2O$, Cs-containing organometallic compounds, CsF, $Cs_2O$, and $Cs_2CO_3$ can also be deposited as an electron injection layer between the organic layer and the cathode layer to lower the operating voltage.

It is known to have other layers in organic electronic devices. For example, there can be a layer (not shown) between the anode 110 and buffer layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

In some embodiments, the device comprises:
an anode;
a hole injection layer comprising a conductive polymer and a fluorinated acid polymer;
a photoactive layer comprising an electroluminescent material and a phenanthroline derivative host material having Formula I;
an electron transport layer comprising a metal quinolate derivative;
an electron injection layer comprising a material selected from the group consisting of Li-containing organometallic compounds, LiF, $Li_2O$, Cs-containing organometallic compounds, CsF, $Cs_2O$, and $Cs_2CO_3$; and
a cathode.

In some embodiments, the above device further comprises a hole transport layer between the hole injection layer and the photoactive layer. In some embodiments of the above device, the phenanthroline derivative of Formula I has $R^1$ selected from the group consisting of biphenyl, naphthyl, naphthylphenyl, triphenylamino, and carbazolylphenyl. In some embodiments, the phenanthroline derivative of Formula I has $R^1$=phenyl and $R^2$=$R^3$ where $R^2$ and $R^3$ are selected from the group consisting of biphenyl, naphthylphenyl, and arylanthracenyl. In some embodiments, the phenanthroline derivative of Formula I has $R^1$=phenyl, $R^2$=H and $R^3$ is selected from the group consisting of phenyl, biphenyl, naphthylphenyl, arylanthracenyl, triphenylamino, and carbazolylphenyl.

In some embodiments, the device comprises:
an anode;
a hole injection layer comprising a conductive polymer and a fluorinated acid polymer;
a photoactive layer comprising an electroluminescent material and a host material;
an electron transport layer comprising a phenanthroline derivative having Formula I;
an electron injection layer comprising a material selected from the group consisting of Li-containing organometallic compounds, LiF, $Li_2O$, Cs-containing organometallic compounds, CsF, $Cs_2O$, and $Cs_2CO_3$; and
a cathode.

In some embodiments, the above device further comprises a hole transport layer between the hole injection layer and the photoactive layer. In some embodiments of the above device, the phenanthroline derivative of Formula I has $R^1$ selected from the group consisting of biphenyl, naphthyl, naphthylphenyl, triphenylamino, and carbazolylphenyl. In some embodiments, the phenanthroline derivative of Formula I has $R^1$=phenyl and $R^2$=$R^3$ where $R^2$ and $R^3$ are selected from the group consisting of naphthylphenyl, arylanthracenyl, triphenylamino, and carbazolylphenyl. In some embodiments, the phenanthroline derivative of Formula I has $R^1$=phenyl, $R^2$=H and $R^3$ is selected from the group consisting of phenyl, biphenyl, naphthylphenyl, arylanthracenyl, triphenylamino, and carbazolylphenyl.

d. Device Fabrication

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

In some embodiments, the device is fabricated by liquid deposition of the buffer layer, the hole transport layer, and the photoactive layer, and by vapor deposition of the anode, the electron transport layer, an electron injection layer and the cathode.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, comprising the new compounds, includes, but not limited to, chlorinated hydrocarbons (such as methylene chloride, chloroform, chlorobenzene), aromatic hydrocarbons (such as substituted and non-substituted toluenes and xylenes), including trifluorotoluene), polar solvents (such as tetrahydrofuran (THP), N-methylpyrrolidone) esters (such as ethylacetate) alcohols (isopropanol), keytones (cyclopentatone) and mixtures thereof. Suitable solvents for photoactive materials have been described in, for example, published PCT application WO 2007/145979.

EXAMPLES

The concepts described herein will be further described in the following examples, which do not limit the scope of the invention described in the claims.

Example 1

Example 1 demonstrates the preparation of an intermediate dichlorobathophenanthroline compound, 2,9-dichloro-4,7-diphenyl-1,10-phenanthroline.

a) The procedure from Yamada et al Bull Chem Soc Jpn, 63, 2710, 1990 was used to prepare the trimethylene bridged bathophenanthroline as follows: 2 g of bathophenanthroline was taken into 20 g 1,3-dibromopropane and refluxed under air. After about 30 mins the dense orange slurry was cooled. Methanol was added to dissolve the solids, and then acetone was added to precipitate a bright orange solid. This was filtered and washed with toluene and dichloromethane ("DCM") resulting in an orange powder in 2.8 g yield.

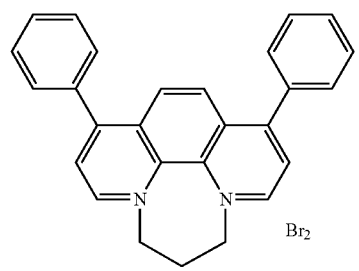

$C_{27}H_{22}Br_2N_2$
Exact Mass: 532.01
Mol. Wt.: 534.29
C, 60.70; H, 4.15; Br, 29.91; N, 5.24 b) 2.8 g of product from above was dissolved into 12 mL water and dripped into an ice-cooled solution of 21 g potassium ferricyanide and 10 g sodium hydroxide in 30 mL water over the course of about 30 mins, and then stirred for 90 mins. This was iced again and neutralized with 60 mL of 4M HCl to a pH of about 8. The pale tan/yellow solid was filtered off and suctioned dry. The filtered solid was placed in a soxhlet and extracted with chloroform to extract a brown solution. This was evaporated to a brownish oily solid and then washed with a small amount of methanol to give a pale brown solid (~1.0 g 47%). The product may be recrystallized from chloroform/methanol as golden platelets by evaporating out the chloroform from the mixture. The structure was identified by NMR as the diketone below.

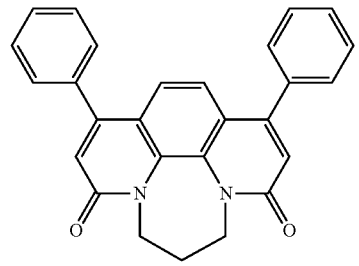

$C_{27}H_{20}N_2O_2$
Exact Mass: 404.15
Mol. Wt.: 404.46
C, 80.18; H, 4.98; N, 6.93; O, 7.91 c) Combined portions of diketone from step (b) above totaling 5.5 g (13.6 mM) were suspended in 39 mL $POCl_3$ and 5.4 g $PCl_5$ was added. This was degassed and refluxed under nitrogen for 8 hrs. The excess POCl3 was removed by evaporation. Ice was added to decompose the remaining chlorides and the mixture was neutralized with ammonia solution. The brown precipitate was collected and dried under vacuum while the mother liquor was extracted with methylene chloride. All brown material was combined, evaporated to a brown gum and methanol added. After shaking and stirring a pale yellow solid was isolated which recrystallized as off-white needles from CHCl3 and methanol (1:10). Analysis by NMR indicated the dichlorobathophenanthroline structure below.

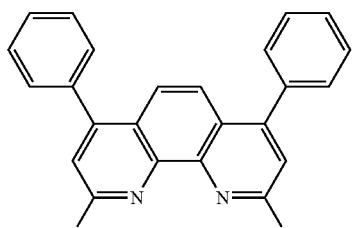

C$_{24}$H$_{14}$Cl$_2$N$_2$
Exact Mass: 400.05
Mol. Wt.: 401.29
C, 71.82; H, 3.52; Cl, 17.67; N, 6.98

Example 2

Example 2 illustrates the preparation of phenanthroline derivative Compound 3, using Suzuki coupling of 2,9-dichloro-4,7-diphenyl-1,10-phenanthroline from Example 1 with 4-(1-naphthyl)-phenylboronic acid To 2.0 g of dichlorobathophenanthroline (5 mM) from Example 1 was added 2.6 g (11 mM) boronic acid in a glove box. To this was added 0.15 g tris(dibenzylideneacetone) dipalladium (0) ("Pd2 DBA3") (0.15 mM), 0.1 g tricyclohexylphosphine (0.35 mM), and 3.75 g potassium phosphate (17 mM), and all were dissolved into 30 mL dioxane and 15 mL water. This was mixed and heated in a glove box at 100° C. for 1 hr, then warmed gently (minimum rheostat setting) under nitrogen overnight. On reaching about 80° C. the mixture was a tan brown slurry which slowly became clear brown with a dense precipitate. As the solution refluxed (air condensor) a white fibrous precipitate formed. This was cooled and the white fibers were filtered from the dioxane after adding additional water. The fibers were dissolved into chloroform and then evaporated and precipitated in toluene by adding methanol, as off white powder. This was collected by filtration and washed well with methanol to isolate ~2.75 g of Compound 3.

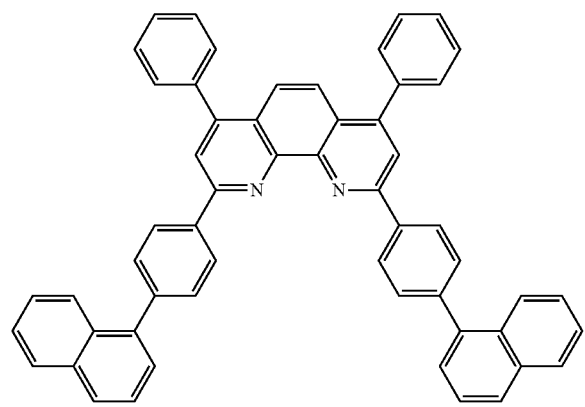

Example 3

This example illustrates the preparation of phenanthroline derivative Compound 4, using Suzuki coupling of 2,9-dichloro-4,7-diphenyl-1,10-phenanthroline from Example 1 with 4-triphenylaminoboronic acid.

To 2.0 g of dichlorobathophenanthroline (5 mM) from Example 1 was added 3.0 g (11 mM) boronic acid. To this was added 0.15 g Pd2 DBA3 (0.15 mM), 0.1 g tricyclohexylphosphine (0.35 mM) and 3.75 g potassium phosphate (17 mM), and all were dissolved into 30 mL dioxane and 15 mL water. This was mixed and heated in a glove box at 100° C. for 1 hr, then warmed gently (minimum rheostat setting) under nitrogen overnight. On reaching about 80° C. the mixture was a tan brown slurry which slowly became clear brown with a dense precipitate. As the solution refluxed (air condensor) a white powdery precipitate formed. The mixture was cooled and removed from the glove box. The dioxane was removed by evaporation and additional water added. A light brown gummy solid was isolated by filtration and washed with water. The solid dissolved well in toluene and dichloromethane. The product was Compound 4.

Compound 4

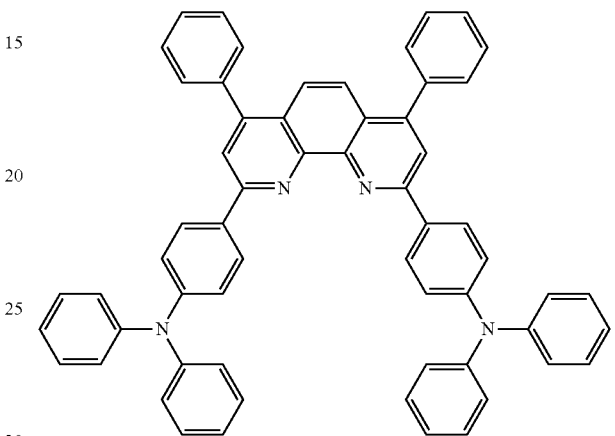

Example 4

This example illustrates the preparation of phenanthroline derivative Compound 9, using Suzuki coupling of 2,9-dichloro-4,7-diphenyl-1,10-phenanthroline from Example 1 with the boronic ester shown below.

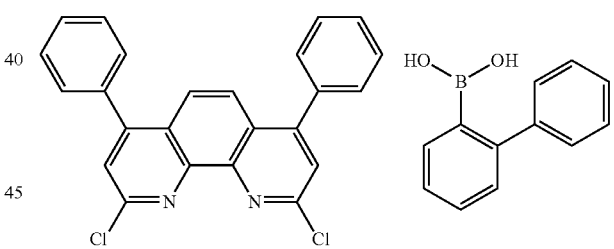

Take 2.0 g of dichloro-phen (5 mM) in glove box and add 2.0 g (11 mM) boronic ester (Aldrich). Add 0.15 g Pd2 DBA3 (0.15 mM), 0.1 g tricylohexylphosphine (0.35 mM) and 3.75 g potassium phosphate (17 mM) and dissolve all into 30 mL dioxane and 15 mL water. Mix and heat in glove box in mantle at 100 C for 1 hr then warm gently (minimum rheostat setting) under nitrogen overnight. Solution immediately is dark purple but on reaching ~80 C it is a tan brown slurry which slowly becomes clear brown. As the solution cools a flocculent ppt forms. Cool and work up by removing from glove box and adding more water. Separate the aqueous and organic layers and wash aq layer with DCM. Combine all organic layers, dry on anhydrous magnesium sulfate and filter through a silica plug. Collect the orange solution which was evaporated to low volume and methanol was added to ppt a pale orange solid. Dissolve in hot toluene and run through a florisil column eluting a pale yellow band with toluene and then DCM. Evaporate to low volume and add methanol to ppt a crystalline white solid. Isolate ~2.55 g material. The structure was confirmed by NMR analysis as Compound 9

Compound 9

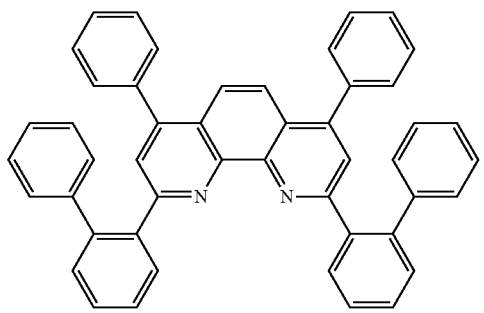

Example 5

This example illustrates the preparation of phenanthroline derivative Compound 10, using Suzuki coupling of 2,9-dichloro-4,7-diphenyl-1,10-phenanthroline from Example 1 with the boronic ester shown below.

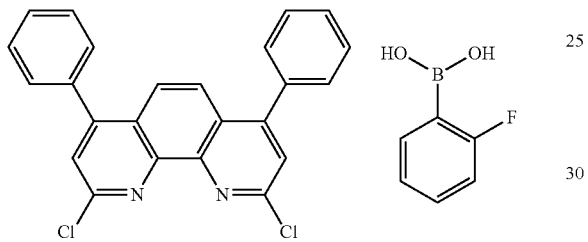

Take 2.0 g of dichloro-phen (5 mM) in glove box and add 1.5 g (11 mM) boronic acid. Add 0.15 g Pd2 DBA3 (0.15 mM), 0.1 g tricyclohexylphosphine (0.35 mM) and 3.75 g potassium phosphate (17 mM) and dissolve all into 30 mL dioxane and 15 mL water. Mix and heat in glove box in mantle at 100 C for 1 hr then warm gently (minimum rheostat setting) under nitrogen overnight. Solution immediately is dark purple but on reaching ~80 C it is a clear brown solution which slowly becomes clear brown with a dense ppt. As the solution refluxes (air condensor) a white fibrous ppt forms. Cool and work up by removing from glove box and filter off white fibers from the dioxane after adding more water. Dissolve into chloroform and then chromatograph on basic alumina eluting with chloroform as fast running blue PL band and evaporate as creamy white needles. Collect by filtration and wash well with methanol then redissolve in toluene as a pale yellow solution and chromatograph on florisil eluting with toluene to isolate ~1.6 g white crystalline material after evaporation and addition of methanol. Solid has deep blue/purple PL. The structure was confirmed by NMR analysis as Compound 10:

Compound 10

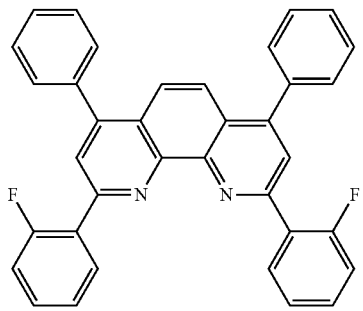

Example 6

This example illustrates the preparation of phenanthroline derivative Compound 11, using Suzuki coupling of 2,9-dichloro-4,7-diphenyl-1,10-phenanthroline from Example 1 with the boronic ester shown below.

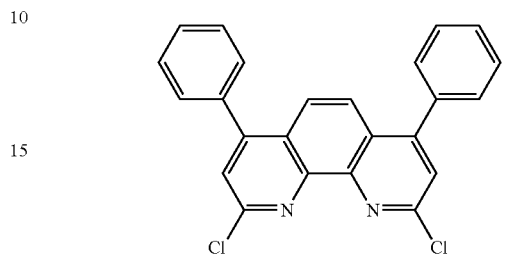

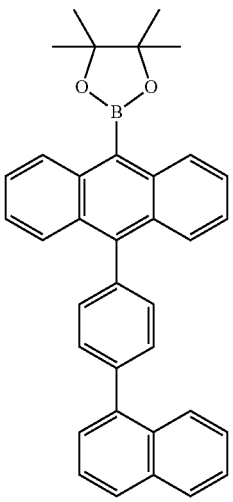

Take 1.0 g of dichloro-phen (2.5 mM) in glove box and add 2.6 g (5.5 mM) boronic ester. Add 0.15 g Pd2 DBA3 (0.15 mM), 0.1 g tricyclohexylphosphine (0.35 mM) and 3.75 g potassium phosphate (17 mM) and dissolve all into 30 mL dioxane and 15 mL water. Mix and heat in glove box in mantle at 100 C for 1 hr then warm gently (minimum rheostat setting) under nitrogen overnight. Solution immediately is dark purple but on reaching ~80 C it is a tan brown slurry which slowly becomes clear brown. As the solution cools a flocculent ppt forms. Cool and work up by removing from glove box and adding more water. Separate the aqueous and organic layers and wash aq layer with DCM. Combine all organic layers, dry on magnesium sulfate and filter through a silica plug. Collect the orange solution which was evaporated to low volume and methanol added to ppt a pale orange solid. Dissolve in hot toluene/DCM and run through a silica/florisil/B-alumina stacked column eluting with DCM/Toluene as a pale yellow solution. Material is strongly colored on the chromatographic medium. —especially florisil. Evaporate to low volume and add methanol to ppt a yellow solid. isolate ~2.55 g material. The structure was confirmed by NMR analysis to be Compound 11:

Compound 11

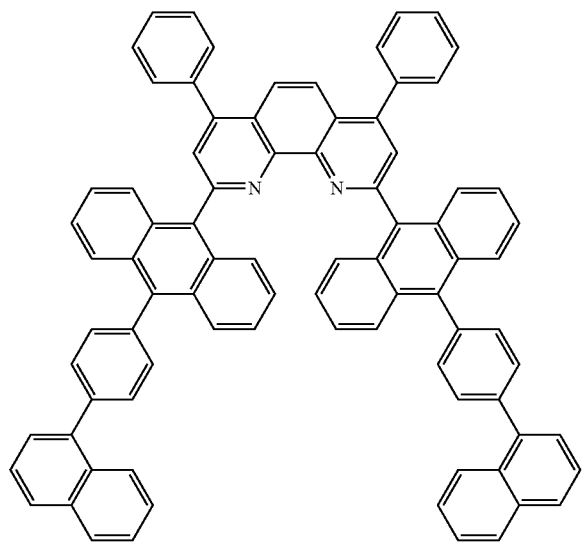

Example 7

This example illustrates the preparation of phenanthroline derivative Compound 12, using Suzuki coupling of 2,9-dichloro-4,7-diphenyl-1,10-phenanthroline from Example 1 with the boronic ester shown below.

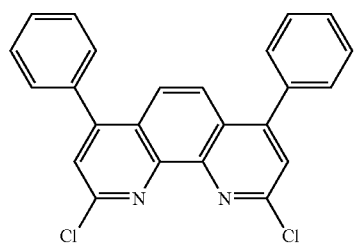

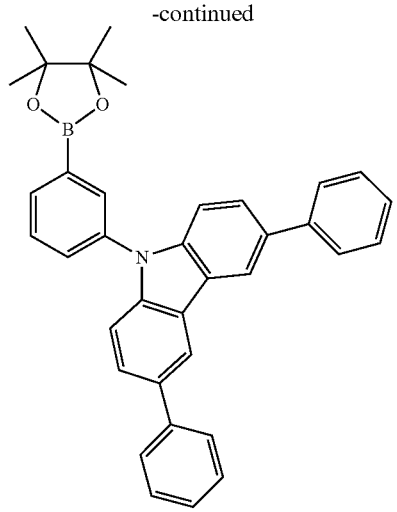

Take 1.0 g of dichloro-phen (2.5 mM) in glove box and add 3.12 g (6 mM) boronic ester. Add 0.15 g Pd2 DBA3 (0.15 mM), 0.1 g tricyclohexylphosphine (0.35 mM) and 2.0 g potassium phosphate (9 mM) and dissolve all into 30 mL dioxane and 15 mL water. Mix and heat in glove box in mantle at 100 C for 1 hr then warm gently (minimum rheostat setting) under nitrogen overnight. Solution immediately is dark purple but on reaching ~80 C it is a tan brown slurry which slowly becomes clear brown with a dense ppt. As the solution refluxes (air condensor) a brown gummy material forms. Cool and work up by removing from glove box and add water. Extract into DCM and dry over magnesium sulfate. Chromatograph on a plug of silica/florisil eluting with DCM then DCM/methanol 2:1. Collect a pale yellow solution which was evaporated and upon addition of methanol ppts a white/pale yellow solid. The structure was confirmed by NMR analysis to be Compound 12:

Compound 12

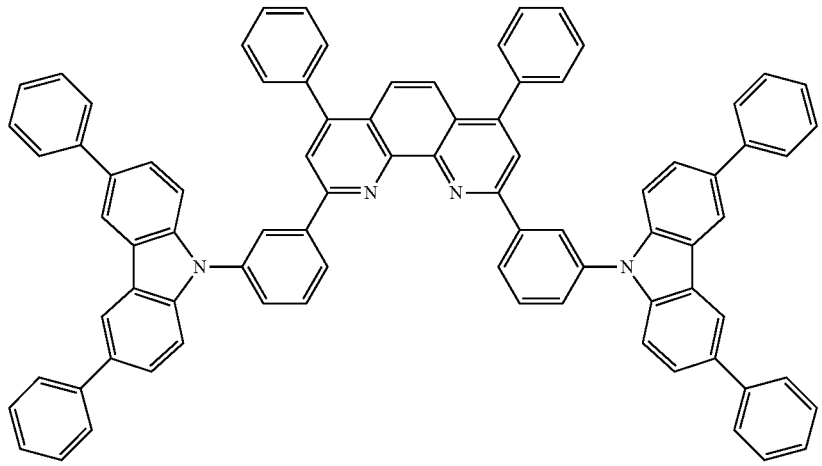

Example 8

This example illustrates the preparation of phenanthroline derivative Compound 13, using Suzuki coupling of 2,9-dichloro-4,7-diphenyl-1,10-phenanthroline from Example 1 with the boronic ester shown below.

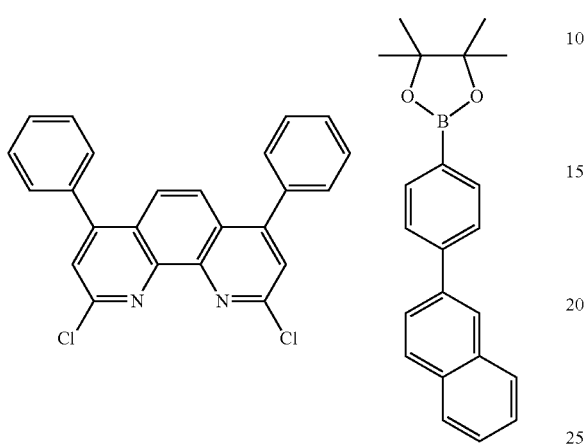

Take 2.0 g of dichloro-phen (5 mM) in glove box and add 3.4 g (11 mM) boronic acid. Add 0.15 g Pd2 DBA3 (0.15 mM), 0.1 g tricyclohexylphosphine (0.35 mM) and 3.75 g potassium phosphate (17 mM) and dissolve all into 30 mL dioxane and 15 mL water. Mix and heat in glove box in mantle at 110 C for 1 hr then warm gently (minimum rheostat setting) under nitrogen overnight. Solution immediately is dark purple but on reaching ~80 C it is a tan brown slurry which slowly becomes clear brown with a dense ppt. As the solution refluxes (air condensor) a white fibrous ppt forms. Cool and work up by removing from glove box and filter off white fibers from the dioxane after adding more water. Dissolve into chloroform and then evaporate and ppt in toluene by adding methanol as off white fine needles. Collect by filtration and wash well with methanol to isolate ~2.25 g material. The structure was confirmed by NMR analysis as Compound 13:

Compound 13

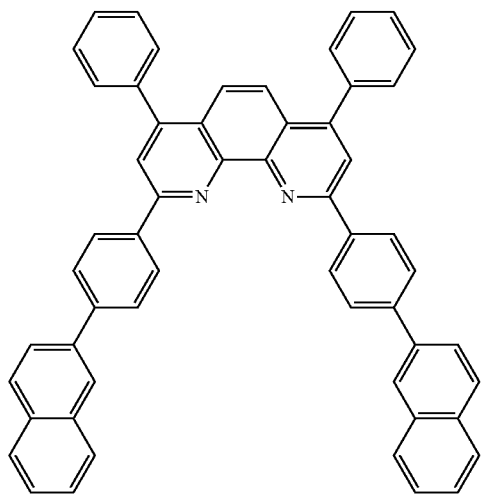

Example 9

This example illustrates the preparation of phenanthroline derivative Compound 1, using Suzuki coupling of 2,9-dichloro-4,7-diphenyl 1,10-phenanthroline from Example 1 with the boronic ester shown below.

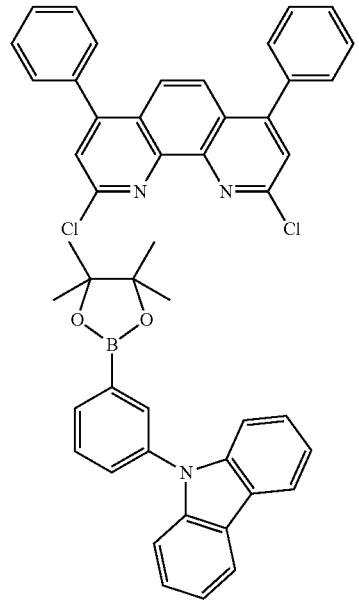

Take 2.0 g of dichloro-phen (5 mM) in glove box and add 4.0 g (11 mM) boronic ester. Add 0.15 g Pd2 DBA3 (0.15 mM), 0.1 g tricyclohexylphosphine (0.35 mM) and 3.75 g potassium phosphate (17 mM) and dissolve all into 30 mL dioxane and 15 mL water. Mix and heat in glove box in mantle at 110 C for 1 hr then warm gently (minimum rheostat setting) under nitrogen overnight. Solution immediately is dark purple but on reaching ~80 C it is a tan brown slurry which slowly becomes clear brown with a dense ppt. As the solution refluxes (air condensor) a flocculent ppt forms. Cool and work up by removing from glove box and filter off white fibers from the dioxane after adding more water. Dissolve into chloroform and then evaporate and ppt in toluene by adding methanol as off white fine needles. Collect by filtration and wash well with methanol to isolate ~3.55 g material. The structure was confirmed by NMR analysis as Compound 1:

Compound 1

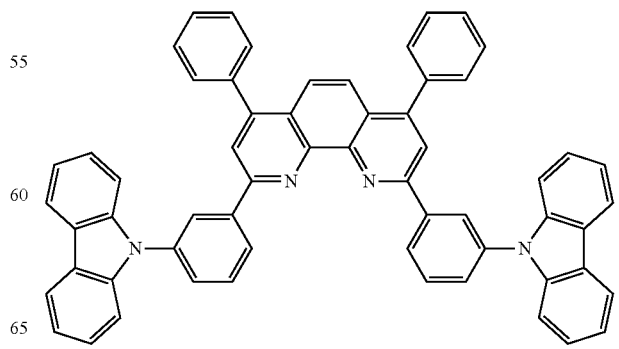

The properties of Compound 1 were as follows:
- Tg=172° C.
- photoluminescence peak (2% in toluene)=406 nm
- UV/Vis peaks=341, 293 nm
- electroluminescent emissive peak=405 nm

Example 10

This example illustrates the preparation of phenanthroline derivative Compound 14, using Suzuki coupling of 4,7-dichloro-1,10-phenanthroline with the boronic ester shown below.

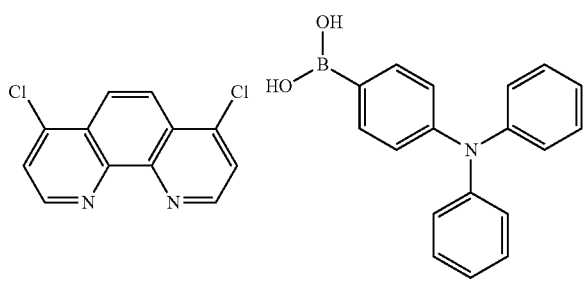

Take 2.0 g of dichloro-phen (8 mM) in glove box and add 4.7 g (17 mM) boronic acid. Add 0.15 g Pd2 DBA3 (0.15 mM), 0.1 g tricyclohexylphosphine (0.35 mM) and 3.75 g potassium phosphate (17 mM) and dissolve all into 30 mL dioxane and 15 mL water. Mix and heat in glove box in mantle at 100 C for 1 hr then warm gently (minimum rheostat setting) under nitrogen overnight. Solution immediately is dark purple but on reaching ~80 C it is a tan brown slurry which slowly becomes clear brown. As the solution refluxes (air condensor) it remains clear brown. Cool and work up by removing from glove box and evaporate out the dioxane then add more water. Filter off light brown gummy solid and wash with water. Solid dissolves well in toluene and DCM. The structure was confirmed by NMR analysis to be Compound 14:

Compound 14

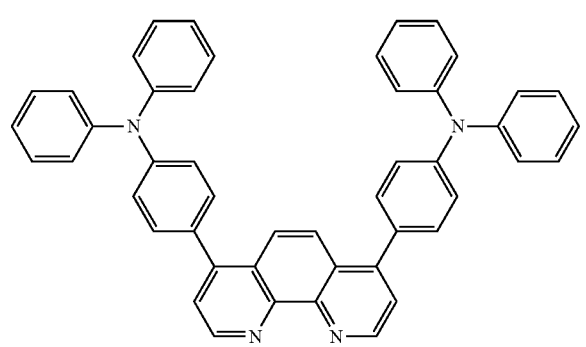

Example 11

This example illustrates the preparation of phenanthroline derivative Compound 15, using Suzuki coupling of 4,7-dichloro-1,10-phenanthroline with the boronic ester shown below.

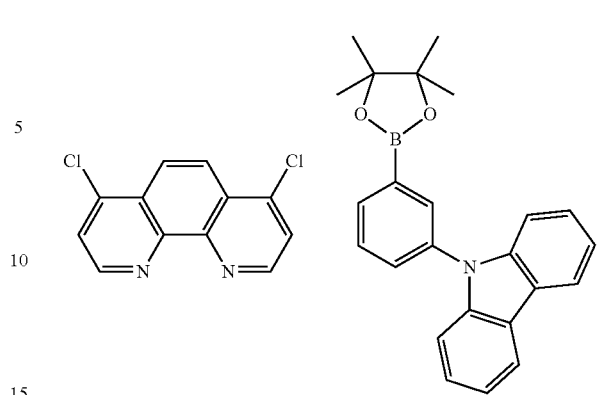

Take 2.5 g of dichloro-phen (10 mM) in glove box and add 8.0 g (22 mM) boronic ester. Add 0.30 g Pd2 DBA3 (0.30 mM), 0.2 g tricylcohexylphosphine (0.70 mM) and 7.5 g potassium phosphate (34 mM) and dissolve all into 60 mL dioxane and 30 mL water. Mix and heat in glove box in mantle at 100 C for 1 hr then warm gently (minimum rheostat setting) under nitrogen overnight. Solution immediately is dark purple but on reaching ~80 C it is a tan brown slurry which slowly becomes clear brown. As the solution refluxes (air condensor) no ppt forms. Cool and work up by removing from glove box and filter off orange gum from the dioxane after adding more water (on celite). Dissolve into chloroform and then chromatograph on column of silica/florisil/alumina (B) and elute with DCM (elutes blue PL fraction in very low amount as a pale yellow solution). Change to 50:50 methanol/DCM and elute orange solution which appears to be bulk of the material. Product seems to be extremely soluble but 'crystallizes' as a white powder from acetone/methanol/DCM mixture. Recover ~5.6 g of white product sent for nmr in DCM (colorless solution with blue PL). The structure was confirmed by NMR analysis as Compound 15:

Compound 15

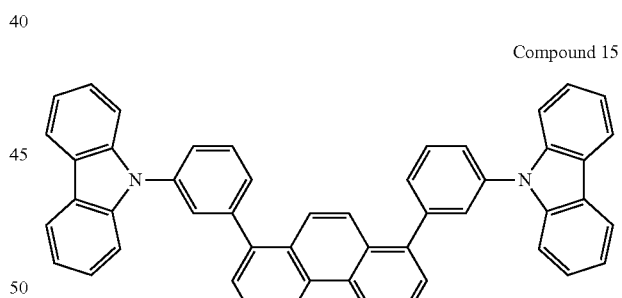

Example 12

This example illustrates the preparation of phenanthroline derivative Compound 17.

To stirring 2,4,7-phenyl-1,10-phenanthroline (2 grams) in THF (20 ml), 1-naphthalmagnesiumbromide (0.0130 mol in THF) was added and refluxed. The mixture was cooled and treated with water and chloroform seperation. The organic mixture was treated with MnO2 and filtered. The resulting material was purified by silica column chromatography with hexanes and DCM then recrystallized from toluene yielding 0.467 g product. The structure was confirmed by NMR analysis as Compound 17:

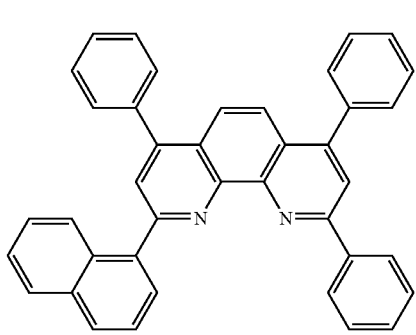

Compound 17

Example 13

This example illustrates the preparation of phenanthroline derivative Compound 18.

To stirring 2,4,7-phenyl-1,10-phenanthroline (2 g, 0.0049 mol) and 20 ml THF, 2-naphthylmagnesiumbromide was added (3 g, 0.0130 mol in THF) and refluxed overnight The mixture was cool and water added and extracted into organic solvent and treated with 91 g MnO2 and filtered and concentrated when a solid precipitated from solution this precipitate was recrystallized from toluene yielding 260 mg. The structure was confirmed by NMR analysis to be Compound 18:

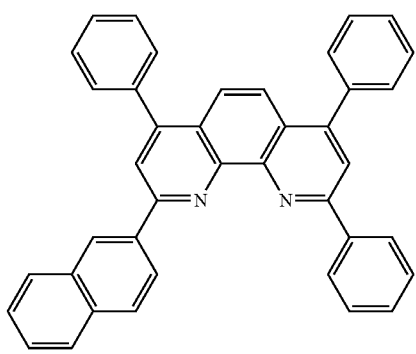

Compound 18

Example 14

This example illustrates the preparation of phenanthroline derivative Compound 19.

To 4,7-dichlorophenanthroline (1.245 g, 0.0050 mol) and the 3-boronate ester of triphenylamine (4.1 g, 0.0111 mol), Pd2/DBA3 (0.3 g) and tricyclohexyl phosphine (0.21 g) in 30 ml 1,4-dioxane was added followed by 4.75 g K3PO4 in 15 ml of water and refluxed overnight. Cooled and performed water/Chloroform extraction of mixture. recrystallized from DCM/hexanes, then silica chromatography using CHCl3/MeOH concentrated heart cuts almost all the way and filtered for 1.6 grams Yield is 89%. The structure was confirmed by NMR analysis to be Compound 19:

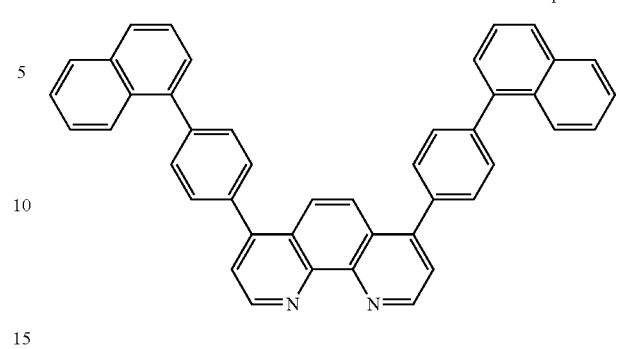

Compound 19

Example 15

This example illustrates the preparation of phenanthroline derivative Compound 20.

To 4,7-dichlorophenanthroline (1.245 g, 0.0050 mol), and 4-(1-naphthyl)phenylboronic acid (5.5 g, 0.0111 mol), Pd2/DBA3 (0.3 g) and tricyclohexyl phosphine (0.21 g) in 30 ml 1,4-dioxane was added followed by 4.75 g K3PO4 in 15 ml of water and refluxed overnight. Cooled and performed water/DCM extraction of mixture. Major fractions were recrystallized from DCM and methanol then filtered and dried to 2.23 g, 67% yield. The structure was confirmed by NMR analysis to be Compound 20:

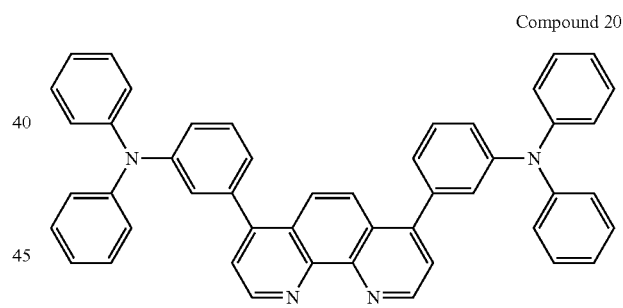

Compound 20

Example 16

This example illustrates the preparation of phenanthroline derivative Compound 2.

Phenyllithium (0.0384 mol), 1.8 mol/dibutylether was added to 4,7-bis(4-diphenylaminophenyl)-1,10-phenanthroline (11.647 g, 0.0175 mol) (compound 14 described above) in 456 ml toluene. Reaction is complete at room temperature within an hour. Added 121 g ice, extracted into DCM and treated with 200 g MnO2, purified by silica column chromatography in ethylacetate/hexanes, triturated in ethanol once then with toluene also ran basic alumina plug with chloroform and toluene and dried to 2 grams. The structure was confirmed by NMR analysis to be Compound 2:

Compound 2

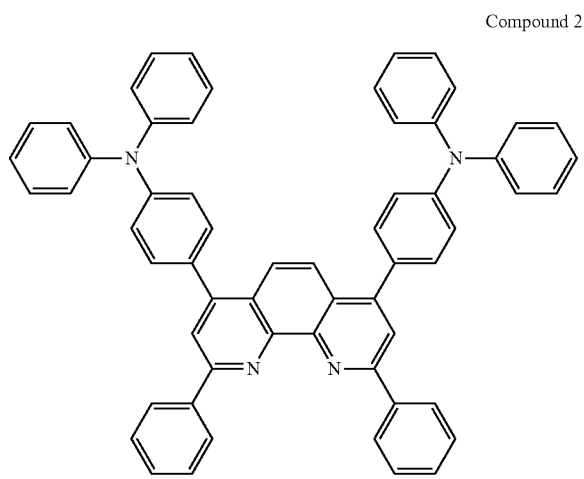

Compound 16

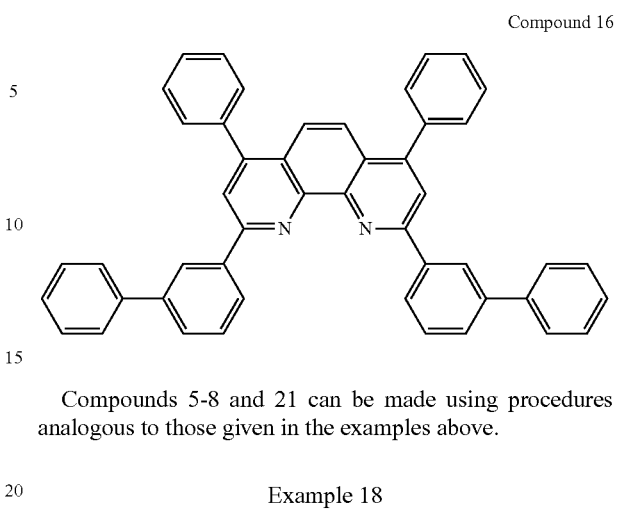

Compounds 5-8 and 21 can be made using procedures analogous to those given in the examples above.

Example 17

This example illustrates the preparation of phenanthroline derivative Compound 16, using Suzuki coupling of 2,9-dichloro-4,7-diphenyl-1,10-phenanthroline from Example 1 with the boronic ester shown below.

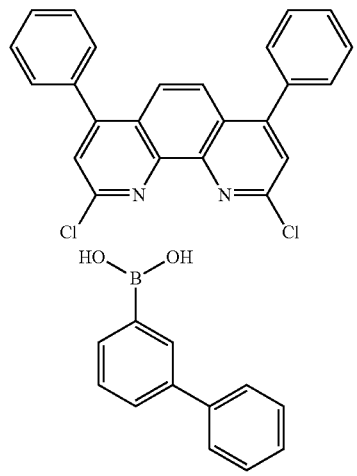

Take 2.0 g of dichloro-phen (5 mM) in glove box and add 2.2 g (11 mM) boronic acid. Add 0.15 g Pd2 DBA3 (0.15 mM), 0.1 g tricyclohexylphosphine (0.35 mM) and 3.75 g potassium phosphate (17 mM) and dissolve all into 30 mL dioxane and 15 mL water. Mix and heat in glove box in mantle at 100 C for 1 hr then warm gently (minimum rheostat setting) under nitrogen overnight. Solution immediately is dark purple but on reaching ~80 C it is a tan brown slurry which slowly becomes clear brown with a dense ppt. As the solution refluxes (air condensor) a white fibrous ppt forms. Cool and work up by removing from glove box and filter off white fibers from the dioxane after adding more water. Dissolve into chloroform and then evaporate and ppt into toluene as white fluff. Collect by filtration and wash well with methanol to isolate ~2.6 g material. The structure was confirmed by NMR analysis to be Compound 16:

Example 18

This example illustrates the use of the phenanthroline compounds in the electron transport layer of an OLED device.

The following materials were used:

anode=Indium Tin Oxide (ITO), 50 nm hole injection layer (NIL)=Buffer 1, which is an aqueous dispersion of an electrically conductive polymer and a polymeric fluorinated sulfonic acid. Such materials have been described in, for example, published U.S. patent applications US 2004/0102577, US 2004/0127637, and US 2005/0205860.

hole transport layer (HTL)=N,N'-bis(naphthalen-1-yl)-N, N'-bis-(phenyl)benzidine (NPB); 25 nm photoactive layer (PAL)=host H1 with 8% by weight of dopant E1.

electron transport layer (ETL)=the phenanthroline compound listed below electron injection layer (EIL)=LiF, 1 nm cathode=Al, 100 nm The buffer material was applied by spin-coating. The other layers were applied by vapor deposition.

The device thicknesses and results are summarized in Table 2 below.

TABLE 2

Device Results

| Ex. | ETL | Buffer, nm | PAL, nm | EQE @ 1000 nits | Color (x, y) @ 1000 nits |
|---|---|---|---|---|---|
| 18-1 | Cmpd. 21 | 53.2 | 32.4 | 8.35% | (0.141, 0.194) |
| 18-2 | Cmpd. 16 | 52.2 | 32.4 | 9.8% | (0.14, 0.198) |
| 18-3 | Cmpd. 3 | 38.5 | 32.4 | 7% | (0.14, 0.141) |
| 18-4 | Cmpd. 1 | 40.8 | 32.4 | 6.1% | (0.141, 0.159) |
| 18-5 | Cmpd. 5 | 42.0 | 32.4 | 0.9% | (0.165, 0.237) |
| 18-6 | Cmpd. 12 | 42.0 | 32.4 | 5.9% | (0.141, 0.152) |

EQE = quantum efficiency;

x and y refer to color coordinates according to the C.I.E. chromaticity scale (Commission Internationale de L'Eclairage, 1931).

Example 19

This example illustrates the use of the phenanthroline compounds as hosts for photoactive materials in an OLED device. The following materials were used:
anode=ITO, 50 nm
HIL=Buffer 1
HTL=NPB
PAL=host with 8% by weight of dopant, as shown below
ETL=the phenanthroline compound listed below, or MQ1, which is a metal quinolate derivative
EIL=as shown in the table
cathode=Al, 100 nm The buffer material was applied by spin-coating. The other layers were applied by vapor deposition.

The device materials, thicknesses and results are summarized in Table 3 below.

TABLE 3

Device Results

| Ex. | Host | Dopant | HIL (nm) | ETL | EIL | EQE (%) | Color (x, y) @1000 nits |
|---|---|---|---|---|---|---|---|
| 19-1 | Cmpd. 1/NPB (8:2), 40 nm | E10 | 70.5 | MQ1, 30 nm | CsF, 1.5 nm | 19.5 | (0.674, 0.325) |
| 19-2 | Cmpd. 21/NPB (8:2), 40 nm | E7 | 67.2 | MQ1, 30 nm | LiF, 1 nm | 11.7 | (0.656, 0.343) |
| 19-3 | Cmpd. 16/NPB (8:2), 40 nm | E7 | 65.4 | MQ1, 30 nm | LiF, 1 nm | 15.4 | (0.656, 0.344) |
| 19-4 | Cmpd. 12 40 nm | E9 | 69.0 | Cmpd. 12, 30 nm | CsF, 1.5 nm | 10.2 | (0.676, 0.324) |

EQE = quantum efficiency;
x and y refer to color coordinates according to the C.I.E. chromaticity scale (Commission Internationale de L'Eclairage, 1931).

Example 20

This example illustrates the use of the phenanthroline compound described herein in the electron transport layer of an OLED device. A comparative device is made with a prior art phenanthroline derivative.

Comparative Compound A was made according to the procedure given in Tetrahedron Letters, Vol. 23 (50), pp. 5291-5294 (1982).

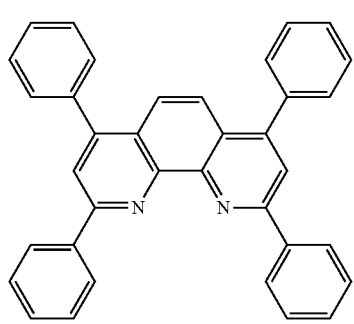

Comparative A

Devices were made with the following configuration:
anode=ITO: 50 nm
HIL=Buffer 1, 40-50 nm
HTL=NPB, 25 nm
PAL=host H1 with 8% by weight of dopant E1
ETL=the phenanthroline compound listed below
EIL=LiF, 1 nm
cathode=Al, 100 nm The buffer material was applied by spin-coating. The other layers were applied by vapor deposition.

The device materials, thicknesses and results are summarized in Table 4 below.

TABLE 4

Device Results

| ETL | Brightness (nits) | V | EQE (%) | cd/A | lm/W | Color (x, y) |
|---|---|---|---|---|---|---|
| Comparative A | 1000 | 4.75 | 9.0 | 9.5 | 6.3 | (0.14, 0.161) |
| Compound 16 | 1000 | 4.4 | 9.85 | 11 | 7.85 | (0.14, 0.188) |
| Comparative A | 4000 | 7.3 | 7.75 | 8.1 | 3.48 | (0.14, 0.160) |
| Compound 16 | 4000 | 6.1 | 8.8 | 9.8 | 5.04 | (0.14, 0.186) |

EQE = quantum efficiency;
x and y refer to color coordinates according to the C.I.E. chromaticity scale (Commission Internationale de L'Eclairage, 1931).

Example 21

This example illustrates the use of the phenanthroline compounds as hosts for photoactive materials in an OLED device, where the photoactive layer is formed by solution processing. The following materials were used:
anode=ITO (180 nm)
buffer layer=Buffer 1 (20 nm)
hole transport layer=HT-1, which is a binaphthalene polymer (20 nm)
photoactive layer=host (as indicated in the table) and dopant E9, in a ratio of 92:8
electron transport layer=a metal quinolate derivative (20 nm)
cathode=LiF/Al (0.5/100 nm)

The buffer material, hole transport material, and photoactive layer material were applied from solutions by sequentially spin-coating and drying each layer. The electron transport layer and cathode were applied by vapor deposition.

The device materials, thicknesses and results are summarized in Table 5 below.

TABLE 5

Device Results

| Example | Host | EQE (%) | cd/A | lm/W | Color (x, y) |
|---|---|---|---|---|---|
| 21-1 | Compound 4 | 10.7 | 8.6 | 4.4 | (0.668, 0.317) |
| 21-2 | Compound 2 | 17.9 | 14.1 | 8.4 | (0.682, 0.316) |

EQE = quantum efficiency;
x and y refer to color coordinates according to the C.I.E. chromaticity scale (Commission Internationale de L'Eclairage, 1931).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A phenanthroline compound selected from the group consisting of

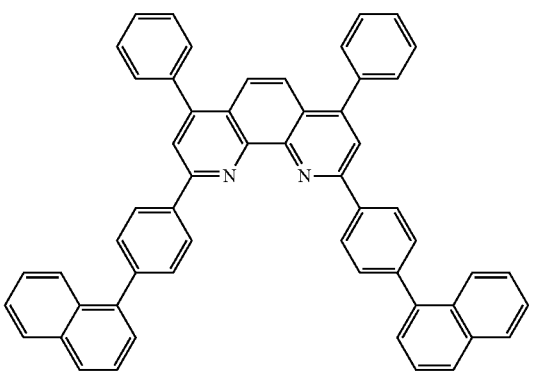

Compound 3

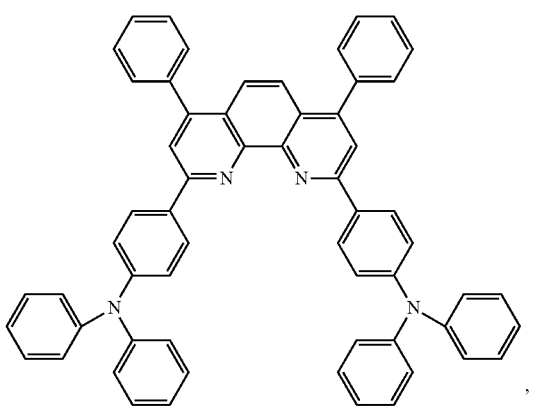

Compound 4

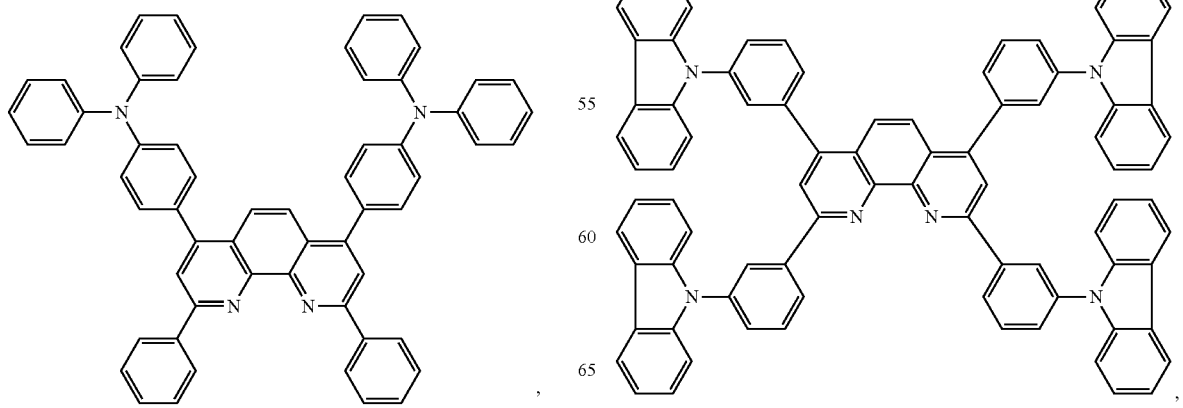

Compound 2, Compound 6

Compound 7
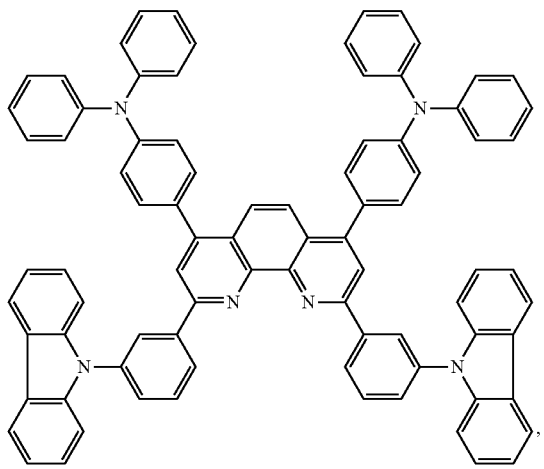
Compound 8
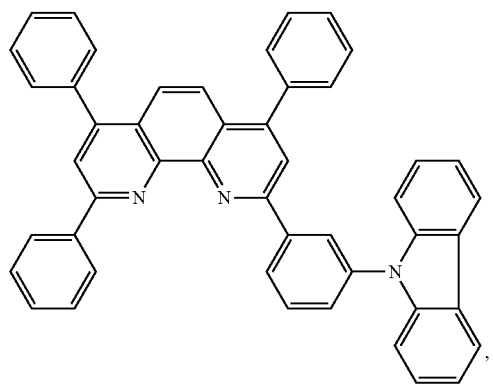
Compound 10
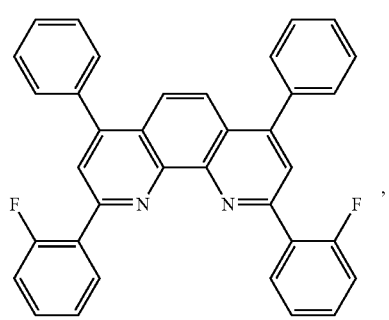
Compound 11
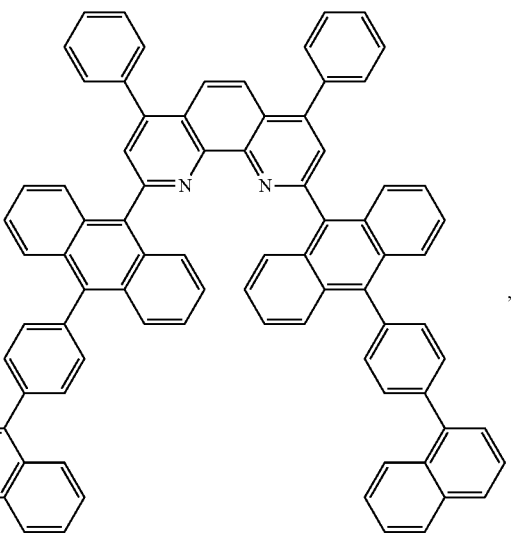
Compound 12
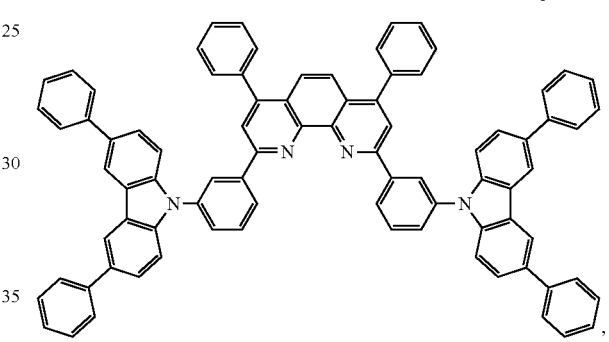
Compound 13
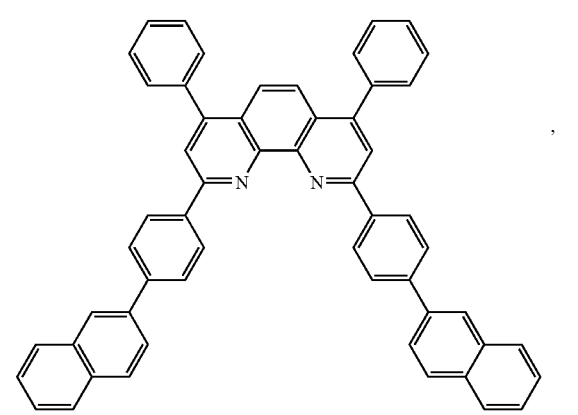
Compound 14
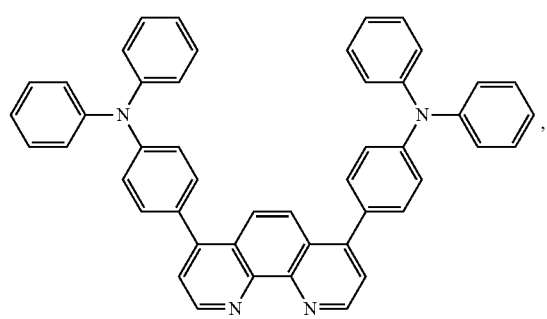

Compound 15
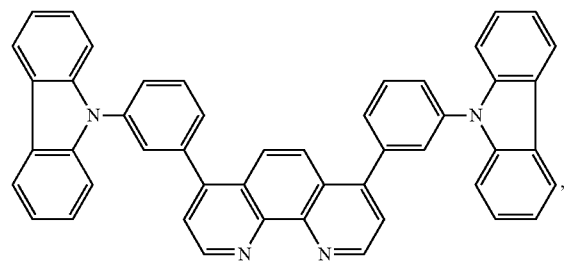
Compound 17
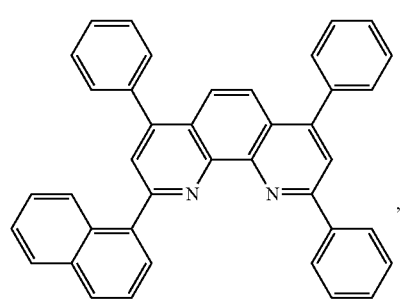
Compound 18
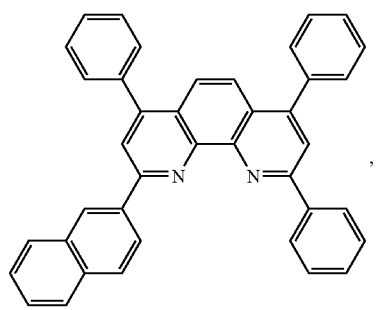
Compound 19
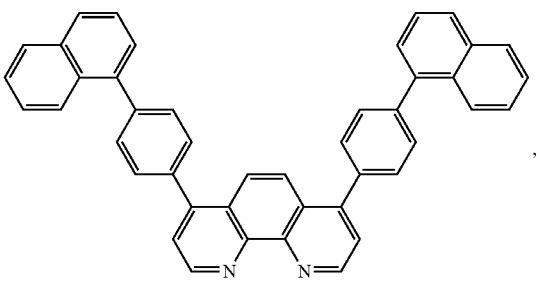
Compound 20
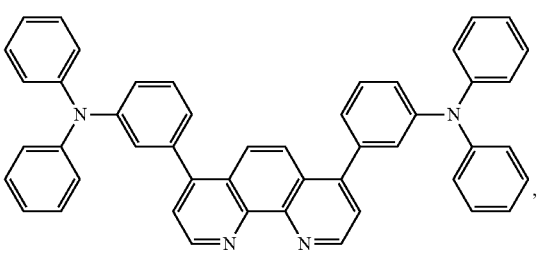
and
Compound 21
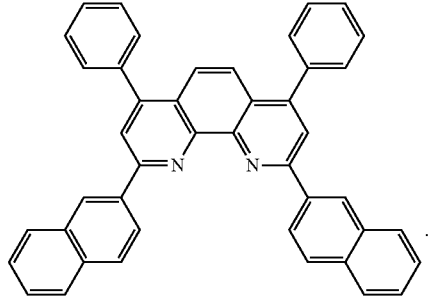
* * * * *